United States Patent
Baek et al.

(10) Patent No.: US 10,273,455 B2
(45) Date of Patent: Apr. 30, 2019

(54) IN VITRO EXPANSION OF ERYTHROID CELLS

(71) Applicant: IUCF-HYU (INDUSTRY-UNIVERSITY COOPERATION FOUNDATION HANYANG UNIVERSITY), Seoul (KR)

(72) Inventors: Eun Jung Baek, Seoul (KR); Eun-Mi Lee, Gyeonggi-do (KR)

(73) Assignee: IUCF-HYU, Seoul (KR)

( * ) Notice: Subject to any disclaimer, the term of this patent is extended or adjusted under 35 U.S.C. 154(b) by 124 days.

(21) Appl. No.: 15/302,647

(22) PCT Filed: Apr. 7, 2015

(86) PCT No.: PCT/KR2015/003483
§ 371 (c)(1),
(2) Date: Oct. 7, 2016

(87) PCT Pub. No.: WO2015/156586
PCT Pub. Date: Oct. 15, 2015

(65) Prior Publication Data
US 2017/0037373 A1  Feb. 9, 2017

(30) Foreign Application Priority Data
Apr. 7, 2014 (KR) .................. 10-2014-0041320

(51) Int. Cl.
*C12N 5/00* (2006.01)
*C12N 5/078* (2010.01)
(52) U.S. Cl.
CPC ...... *C12N 5/0641* (2013.01); *C12N 2501/125* (2013.01); *C12N 2501/14* (2013.01); *C12N 2501/2303* (2013.01); *C12N 2501/39* (2013.01); *C12N 2502/1311* (2013.01); *C12N 2502/1323* (2013.01); *C12N 2502/1358* (2013.01); *C12N 2521/00* (2013.01); *C12N 2531/00* (2013.01)

(58) Field of Classification Search
CPC ... C12N 5/0062; C12N 5/0068; C12N 5/0641
See application file for complete search history.

(56) References Cited

U.S. PATENT DOCUMENTS

| 6,361,998 | B1 | 3/2002 | Bell et al. ............ 435/407 |
| 2003/0194802 | A1 | 10/2003 | Itskovitz-Eldor et al. |
| 2015/0152386 | A1* | 6/2015 | Baek .................. C07K 14/435 435/29 |

FOREIGN PATENT DOCUMENTS

| EP | 2 298 865 A1 | 3/2011 | |
| JP | 2012080874 A | 4/2012 | |
| JP | 2012520672 A | 9/2012 | |
| KR | 10-2013-0055313 | 5/2013 | ............ C12N 5/078 |
| KR | 10-2013-0137574 | 12/2013 | ............ C12N 5/078 |
| WO | WO 2013/147425 | * 3/2013 | ............ C12N 5/078 |
| WO | WO 2014-013255 | 1/2014 | ............ C12N 5/078 |

OTHER PUBLICATIONS

Meuwly et al. "Packed bed bioreactors for mammalian cell culture: Bioprocess and biomedical applications" Biotechnology Advances 25 (2007) 45-56 (Year: 2007).*
International Search Report (ISR) dated Jul. 24, 2015 in PCT/KR2015/003569.
Timmins, N. E. et al., (2009). "Blood cell manufacture: current methods and future challenges". *Trends in Biotechnology.* 27(7):415-422. See abstract pp. 417-418 figures 1-2.
Miyoshi, et al.; "Three-dimensional culture of mouse bone marrow cells within a porous polymer scaffold: effects of oxygen concentration and stromal layer on expansion of haematopoietic progenitor cells", Journal of Tissue Engineering and Regenerative Medicine, J Tissue Eng Regen Med 2011; 5: 112-118. Published online Jul. 23, 2010.
Salati, S., et al.; "Co-Culture of Hematopoietic Stem/Progenitor Cells with Human Osteoblasts Favours Mono/Macrophage Differentiation at the Expense of the Erythroid Lineage", PLOS One | www.plosone.org, Jan. 2013 | vol. 8 | Issue 1 | e53496, pp. 1-10.
Housler, G. J., et al.; "Compartmental Hollow Fiber Capillary Membrane-Based Bioreactor Technology for in Vitro Studies on Red Blood Cell Lineage Direction of Hematopoietic Stem Cells", Tissue Engineering: Part C, vol. 18, No. 2, 2012, pp. 1-10.
Choi, H. S., et al.; "Autonomous control of terminal erythropoiesis via physical interactions among erythroid cells", Stem Cell Research (2013) 10, pp. 442-453.
Baek, E. J., et al.; "Stroma-free mass production of clinical-grade red blood cells (RBCs) by using poloxamer 188 as an RBC survival enhancer". Blood Components, Transfusion, vol. 49, Nov. 2009, pp. 2285-2295.
Extended European Search Report from corresponding European Patent Application No. 15777380.5 dated Jul. 19, 2017.

* cited by examiner

*Primary Examiner* — Ruth A Davis
(74) *Attorney, Agent, or Firm* — Harness, Dickey & Pierce, P.L.C.

(57) ABSTRACT

The present invention relates to a method for in vitro expansion of erythroid cells. The method includes subjecting erythroid cells to 3-dimensional packed cell culture using a porous structure. The use of the composition according to the present invention enables in vitro expansion of erythroid cells in the most efficient manner.

11 Claims, 25 Drawing Sheets

FIG. 13

IN VITRO EXPANSION OF ERYTHROID CELLS

CROSS-REFERENCE TO RELATED APPLICATIONS

This application is a national phase application of PCT/KR2015/003483, filed on Apr. 7, 2015, which claims the benefit of priority to Korean Patent Application No. 10-2014-0041320, filed on Apr. 7, 2014, the disclosure of which is incorporated herein by reference.

FIELD

The present invention was supported by the Ministry of Health and Welfare of the Republic of Korea under Project No. HI10C17400200, which was conducted in the research project entitled "Advanced medical technology development" within the project named "Research on efficient differentiation and mechanism of stem cells into erythroid progenitor cells" by the Industry-Academic Cooperation Foundation, Yonsei University under the management of the Korea Health Industry Development Institute, from Apr. 1, 2013 to Mar. 31, 2014.

The present invention was also supported by the Ministry of Health and Welfare of Republic of Korea under Project No. HI12C0202, which was conducted in the research project entitled "Advanced medical technology development" within the project named "Development of drugs for myelodysplastic syndrome through induction of stem cell differentiation and maturation" by the Industry-Academic Cooperation Foundation, Hanyang University, under the management of the Korea Health Industry Development Institute, from Aug. 1, 2013 to Jul. 31, 2014.

The present invention relates to a method for in vitro expansion of erythroid cells.

BACKGROUND

Recent rapid aging of the population and increasing demand for medical services have led to a supply shortage of transfusable blood and an increase in the amount of blood preparations used. With the prevalence of diseases, such as Creutzfeldt-Jakob disease, malaria, and AIDS, there has been an increasing demand for blood that is safe against infections. Thus, the current worldwide shortage of transfusable blood causes difficulties in the surgery and treatment of patients. This blood shortage will become more serious in the future. According to data from the Korea Institute for Health and Social Affairs (2005), the shortage of blood in South Korea is estimated to be 55.5% of the required amount in 2030. The risk of transfusion-transmitted infections causes serious problems in blood recipients. Enormous costs are incurred in developing examination methods and systems to detect the infection risk but it is impossible to completely detect the infections [1]. For these reasons, there is a continued need to develop safe red blood cells that are produced in vitro.

Approximately 2.1 million units of erythrocyte preparations are used in South Korea annually. This value corresponds to at least about $4 \times 10^{18}$ cells, as calculated under the assumption that $2 \times 10^{12}$ cells are present in one unit. It was reported that at least $3 \times 10^{19}$ cells are required annually to replace erythrocyte transfusion in the United States of America alone (15-million units of $2 \times 10^{12}$ cells each). The largest bioreactor for culture of well-established animal cells, such as CHO cells, can be operated to culture cells at a maximum density of $5 \times 10^{7}$ cells in a volume of 20,000 L. 30,000 batch cultures are theoretically required at this density to produce erythrocytes in the current state of the art [2]. That is, animal cell culture methods designed for cultivation conditions in existing methods and systems, such as static culture, suspension culture, fixed bed reactors, and airlift reactors, are practically impossible to apply to the culture of erythrocytes that requires an astronomical number of cells and media and spaces large enough to accommodate the cells. Packed cell culture is the most efficient in terms of space saving. To the best of our knowledge, however, packed cell culture of erythroblasts for the production of erythrocytes has not previously been reported.

The present research team has demonstrated with mediated adhesion-related signals that erythroid cells exhibit better effects in terms of cell maturation, enucleation rate, cell viability, and myelodysplasia at a high cell density that is created by bringing mature erythroid progenitor cells into physical contact with each other to increase the production efficiency of erythrocytes [3]. Further, the present research team showed that 3D packed cell culture of erythroid cells in a tube is also effective in the production of erythrocytes. Also in other previous studies, attempts have been made to increase the density of cells per volume of the overall medium in 2D plate culture or 3D bioreactors. The present inventors have conducted the first research aimed at inducing direct contact between cells by 3D packing.

Erythroid cells in bone marrow are attached together three-dimensionally to create spaces, called erythroblastic islands, where they are mature and proliferate. Such hematopoietic spaces in bone marrow are divided in thin bony trabeculae to prevent cells from being squashed. Based on the environment of bone marrow, the present inventors have succeeded in finding an optimal packing scale for culture of erythroid cells, a pore size sufficient to support the packing scale, an optimal pore scale of a porous structure for cell culture, and a biocompatible material for the porous structure. The present inventors have also succeeded in optimizing a method for the mass production of erythrocytes by reducing the necrosis of cells caused by 3-dimensional packed cell culture and by packing cells in a spin filter for the supply of fresh media to facilitate the exchange and supply of media during cell culture. This is the first report on 3-dimensional packed cell culture of erythroid cells and is an innovative method for the production of erythrocytes, as in human bone marrow, which requires a minimum culture space and a minimum amount of media.

Papers and patent publications are referenced and cited throughout the specification, the disclosure of which is incorporated herein by reference in its entirety in order to more clearly disclose the invention and the state of the art to which the invention pertains.

DISCLOSURE

Technical Problem

The present inventors have earnestly conducted research to develop a method for in vitro expansion of erythroid cells, and as result, have found that 3-dimensional packed cell culture of erythroid cells in a porous structure is highly effective in in vitro expansion of the erythroid cells. The present invention has been accomplished based on this finding.

Therefore, an object of the present invention is to provide a method for in vitro expansion of erythroid cell including subjecting erythroid cells to 3-dimensional packed cell culture using a porous structure.

Other objects and advantages of the invention will become more apparent from the following detailed description, claims, and drawings.

One aspect of the present invention provides a method for in vitro expansion of erythroid cells including subjecting erythroid cells to 3-dimensional packed cell culture using a porous structure.

The present inventors have earnestly conducted research to develop a method for in vitro expansion of erythroid cells, and as result, have found that 3-dimensional packed cell culture of erythroid cells using a porous structure is most efficient in in vitro expansion of the erythroid cells.

As used herein, the term "erythroid cells" includes cells in the stages of maturation from erythroid progenitor cells. The erythroid progenitor cells can be obtained from various sources, for example, peripheral blood, cord blood and bone marrow. CD34+ cells as the erythroid progenitor cells can be isolated by suitable methods known in the art, for example, an immunomagnetic-bead selection method using CD34+ antibody. According to a preferred embodiment of the present invention, the CD34+ cells may be cells derived from cord blood. The erythroid progenitor cells differentiate into mature erythrocytes via erythropoiesis consisting of the following stages: (a) differentiation from hematopoietic stem cells to proerythroblasts; (b) differentiation from the proerythroblasts to basophilic erythroblasts; (c) differentiation from the basophilic erythroblasts to polychromatophilic erythroblasts; (d) differentiation from the polychromatophilic erythroblasts to orthochromatic erythroblasts; (e) differentiation from the orthochromatic erythroblasts to polychromatic erythrocytes; and (f) differentiation from the polychromatic erythrocytes to erythrocytes. Preferably, the erythroid cells used in the present invention include the cells in the maturation stages (d), (e), and (f).

As used herein, the term "erythroid progenitor cells" is intended to include all cells in the stages of erythropoiesis except erythrocytes that complete their maturation stages.

As used herein, the term "3-dimensional packed cell culture" refers to a culture method in which erythroid cells are allowed to settle and packed using a culture vessel, specifically a tube, whose height is large enough so that the erythroid cells can be packed.

As used herein, the term "porous structure" refers to a structure which assists in cell culture due to the presence of a number of pores having a size of several micrometers to several millimeters. The shape and size of the porous structure are not particularly limited and can be appropriately selected depending on the mode and scale of practice of the invention. Materials for the porous structure include, but are not limited to, polyethylene, silica, cellulose, DEAE-dextran, glass, polystyrene plastics, acrylamide, and collagen. Any suitable material that does not adversely affect the cell culture may be used for the porous structure. Specifically, the porous structure may be, for example, a "microcarrier" or "scaffold" structure. The microcarrier refers to a porous support structure for cell culture that has a diameter of about 100 μm to about several mm and includes pores having a size of about 30 to about 500 μm. The use of an assembly of a number of microcarrier units for culture of erythroid cells enables control over culture scale. Specific examples of such microcarriers include Cytopore and Cytoline 1, which were used in the Examples section that follows. The scaffold refers to a support structure for cell culture that includes pores having a size of about several tens to several hundreds of μm. Unlike the microcarrier using an assembly of a number of unit structures, the scaffold is a one-piece structure whose diameter and height are adjusted depending on culture scale. The scaffold may have a pore size of about 10 μm to about 1 mm. The pore size of the scaffold is preferably from 30 μm to 600 μm, more preferably from 30 μm to 500 μm, even more preferably 50 μm to 500 μm, still more preferably 50 μm to 400 μm. The material for the scaffold is not particularly limited and can be selected from metals, ceramics, synthetic polymers, and/or natural polymers. Specific examples of suitable materials for the scaffold include collagen, silk, alginate, polyethylene (PE), poly (lactic acid) (PLA), poly(glycolic acid) (PGA), PLA and PGA copolymers, polytetrafluoroethylene (PTFE), polyvinyl chloride (PVC), polydimethylsiloxane (PDMS), polycaprolactone (PCL), polyurethane (PU), alumina, hydroxyapatite, nickel, titanium, cobalt-chromium alloys, and/or stainless steel. Examples of commercially available products for the scaffold are Honeycomb (KOKEN, Tokyo, Japan) and Biomerix 3D (Biomerix, Fremont, Calif.).

The porous structure per se is porous. Alternatively, the porous structure may be an assembly of subunits including no pores. In this case, gaps exist between the subunits and act like pores of the porous structure. This is contrary to the fact that the porous structure consists of porous subunits. However, gaps between the subunits act like pores that can exert an effect on packed cell culture of erythroid cells. Specifically, the subunits may be beads that have a size sufficient to create gaps of 30 μm to 1500 μm. The material for the beads is not limited. As the subunits, there may also be used microcarrier disks, which were used in the following Examples section.

In one embodiment of the present invention, the porous structure includes pores that has a size distribution of 30 to 1500 μm. The expression "includes pores that has a size distribution of 30 to 1500 μm" is understood that pores outside this range are not excluded. The pore size of 30-1500 μm represents a preferable pore size distribution of the porous microcarrier for expansion of erythroid cells. Some of the pores may be outside this pore size range. The pores may have the same or similar sizes. Alternatively, the pores may have different sizes in the range of 30-1500 μm. The lower limit of the pore size range means the minimum size that allows erythroid cells to enter the pores to create a 3D packing environment. The upper limit of the pore size range is set to provide a similar environment to the bone marrow environment. The pore size distribution is preferably from 30 to 1000 μm, more preferably from 30 to 700 μm, even more preferably from 30 to 500 μm, most preferably from 50 to 500 μm. When the pores have the most preferred size distribution, culture effects are maximized by 3-dimensional packing of erythroid cells.

In one embodiment of the present invention, the porous structure is a macroporous microcarrier. The term "microcarrier" as used herein refers to a support structure for cell culture that has a size of about 100 μm to about several mm. The microcarrier includes a number of pores. The microcarrier can be divided into macroporous, mesoporous, and microporous microcarriers depending on the diameter of the pores. The macroporous structure has an average pore diameter of about 50 μm or more. The mesoporous structure has an average pore diameter of about 2 to about 50 μm and the microporous structure has an average pore diameter of about 2 μm or less. The macroporous microcarrier refers to a microcarrier which includes a number of pores having an average diameter of about 50 μm or more. The present inventors have reached the conclusion that the use of the macroporous carrier is effective for in vitro expansion of erythroid cells. The present inventors have found that the macroporous carrier has a pore size sufficient for 3-dimensional packed cell culture of erythroid cells and can prevent cell squash and difficulty in gas or nutrient exchange, which are problems encountered when packed on an excessively large scale. The gas or nutrient exchange efficiency is maximized by the flowability of the microcarrier. Gas or nutrient can be efficiently exchanged while maintaining an environment for 3-dimensional packed cell culture when the flowable structure is used compared to when a large-scale immobilized structure is used for culture. When it is intended to expand the 3-dimensional packed cell culture scale of erythroid cells to increase the number of erythroid cells per unit bottom area, the porous structure of the microcarrier maintains the cell packing scale optimum. Therefore, the use of the porous microcarrier facilitates extension of the culture scale of erythroid cells.

A culture medium used in the present invention may include general components for culture of animal cells. The culture medium may be a basal medium known in the art. Examples of suitable media include Eagle's minimum essential medium (Eagle's MEM) [Eagle, H. *Science* 130: 142 (1959)], α-MEM [Stanner, C. P. et al., *NAT. New Biol.* 230:52 (1971)], Iscove's MEM [Iscove, N. et al., *J. Exp. Med.* 147:923 (1978)], 199 medium [Morgan et al., *Proc. Soc. Exp. BioMed.,* 73:1 (1950)], CMRL 1066, RPMI 1640 [Moore et al., *J. Amer. Med. Assoc.* 199:519 (1967)], F12 [Ham, Pro. *Natl. Acad. Sci. USA* 53:288 (1965)], F10 [Ham, R. G. *Exp. Cell Res.* 29:515 (1963)], DMEM [Dulbecco's modification of Eagle's medium, Dulbecco, R. et al., *virology* 8:396 (1959)], mixture of DMEM and F12 [Barnes, D. et al., *Anal. Biochem.* 102:225 (1980)], Way-mouth's MB752/I [Waymouth, C. *J. Natl. Cancer Inst.* 22:1003 (1959)], Iscove's modified Dulbecco's medium, Iscove's modified Fisher's medium or Iscove's modified Eagle's medium, McCoy's 5A [McCoy, T. A., et al., *Pro. soc. Exp. Bio. Med.* 100:115 (1959)], MCDB series [Ham, R. G et al., *In vitro* 14:11 (1978)], AIM-V medium, and modified media thereof. A detailed description of the media can be found in R. Ian Freshney, *Culture of Animal Cells*, A Manual of Basic Technique, Alan R. Liss, Inc., New York, the disclosure of which is incorporated herein by reference.

For the purpose of promoting the proliferation and differentiation of erythroid progenitor cells, the medium used in the present invention further includes at least one component selected from the group consisting of stem cell factor (SCF), IL-1, IL-3, IL-4, IL-5, IL-11, granulocyte macrophage-colony stimulating factor (GM-CSF), macrophage colony-stimulating factor (M-CSF), granulocyte-colony stimulating factor (G-CSF), and erythropoietin (EPO). More preferably, the medium used in the present invention includes hydrocortisone, SCF, IL-3, and EPO at the stage of differentiation of proerythroblasts to basophilic erythroblasts, SCF, IL-3, and EPO at the stage of differentiation of basophilic erythroblasts to polychromatophilic erythroblasts, and EPO at the stage of differentiation of polychromatophilic erythroblasts to orthochromatic erythroblasts. The medium does not include cytokine at the stage of differentiation of orthochromatic erythroblasts to polychromatic erythrocytes (i.e. reticulocytes) (i.e. enucleation).

In one embodiment of the present invention, the culture of erythroid cells is performed in a medium to which shear stress is applied by a continuous flow. The "continuous flow" as used herein means that the medium is stirred or exchanged in a regular or irregular cycle or continuously. This continuous flow enables sufficient supply of essential growth elements, including oxygen, to the packed cultured cell layers, assisting in cell expansion.

In one embodiment of the present invention, the continuous flow for culture of erythroid cells is created by stirring. Specifically, the stirring may be performed, for example, using a magnetic stirrer or in a spinner flask.

In one embodiment of the present invention, the flow is created by stirring. The flow is typically created by stirring at 1 to 50 rpm, preferably 1 to 40 rpm, more preferably 5 to 35 rpm, even more preferably 5 to 30 rpm. If the stirring rate (rpm) is higher than the upper limit defined above, excessively high shear stress may be applied to cultured cells, causing the structure of packed cells to collapse and decreased 3-dimensional contact of cells.

In one embodiment of the present invention, the culture is performed in a filter in the medium. The filter is used to prevent erythrocytes from escaping from the porous microcarrier during the continuous flow. The use of the filter minimizes a change in the 3-dimensional packed cell culture environment by shear stress applied to the microcarrier and erythroid cells and enables a smooth flow of the medium, assisting in effective cell expansion.

In one embodiment of the present invention, the filter has a mesh size of 1 to 8 μm. The mesh size of the filter is preferably from 1 to 5 μm, more preferably from 2 to 5 μm, more preferably from 3 to 4 μm. The mesh size of the filter is smaller than the average diameter of erythrocytes. The use of the filter can enhance the flow effect of the medium while preventing erythrocytes from escaping from the pores of the microstructure and floating in the medium. In one embodiment of the present invention, the erythroid cells are cells differentiated from hematopoietic stem cells. Particularly, the erythroid cells are those that almost complete their maturation stages and preferably include those that enter the terminal maturation stage. Erythroid cells undergo enucleation at the end of the terminal maturation stage. Erythroid cells entering the terminal maturation stage are distinguished from hematopoietic stem cells in their characteristics and growth environments. Excellent 3-dimensional packed cell culture effects in the porous microstructure are pronounced in erythroid cells differentiated from hematopoietic stem cells, particularly cells entering the terminal maturation stage. When it is intended to increase the 3-dimensional packed cell culture scale of erythroid cells above an optimum level, many problems may arise, such as cell squash and difficulty in gas or nutrient exchange, causing low cell culture efficiency. Thus, the present inventors have introduced for the first time the use of the porous microcarrier for 3-dimensional packed cell culture of erythroid cells that enables packed cell culture of erythroid cells above an optimum cell density level and can maintain the packed cell culture scale of erythroid cells through the pores of the microcarrier.

In one embodiment of the present invention, the 3D-cultured erythroid cells express at least one adhesion-related gene selected from deleted in liver cancer 1 (DLC 1), intercellular adhesion molecule-4 (ICAM-4), and very late antigen-4 (VLA-4). Intercellular signal exchange is activated by the expression of the adhesion-related genes, resulting in an increase the productivity of erythroid cells. The DLC 1, ICAM-4 and/or VLA-4 protein may also be artificially added to the medium.

In one embodiment of the present invention, erythroid cells are mixed and co-cultured with cells selected from the group consisting of mesenchymal stem cells, endothelial cells, monocytes, macrophages, and histiocytes during the 3-dimensional packed cell culture. Mesenchymal stem cells, endothelial cells, monocytes, macrophages, and histiocytes are constituents of bone marrow and are used to make the environment for culture of erythroid cells similar to the environment of bone marrow. The present inventors have drawn the conclusion that co-culture of erythroid cells with the constituents of bone marrow contributes to maturation of the erythroid cells. When two or more constituents are selected from mesenchymal stem cells, endothelial cells, monocytes, macrophages, and histiocytes, the mixing ratio is not particularly limited but is preferably similar to that in the in vivo environment.

In one embodiment of the present invention, the ratio of the number of cells selected from the group consisting of mesenchymal stem cells, endothelial cells, monocytes, macrophages, and histiocytes to the number of erythroid cells may be from 1:10 to 2:1. The mixing ratio is determined to create a similar environment to the in vivo environment. However, the quantity of erythroid cells may be appropriately increased for the purpose of the present invention, i.e. for culture of erythroid cells.

Advantageous Effects

The features and advantages of the present invention are summarized as follows:

(a) the present invention using a porous structure for 3-dimensional packed cell culture of erythroid cells is effective in in vitro expansion of erythroid cells;

(b) the present invention can markedly improve the in vitro productivity of erythrocytes from erythroid progenitor cells;

(c) the present invention facilitates expansion of the packed cell culture scale of erythroid cells and is effective in maintaining the packed cell culture scale of erythroid cells through the pores of the microcarrier; and (d) the present invention enables the production of clinical grade erythrocytes.

BRIEF DESCRIPTION OF THE DRAWINGS

FIG. 9 shows the proportions of orthochromatic erythroblasts in a control and experimental group II were 39% and 94.1%, respectively, revealing markedly increased cell maturation. Upon 3D packed cell culture in the presence of Cytoline 1, intercellular contact was increased and cell maturation was effective.

FIG. 13 shows images (×200) observed after culture of cells using Cytoline 1 and a filter under different flow conditions at RPM 0 and RPM 25 and Wright-Giemsa staining, the red asterisks, blue arrows, black asterisks, and black arrows indicate enucleated erythroid cells, orthochromatic erythroblasts, dead cells, and polychromatic erythroblasts, respectively.

FIG. 16 shows images (×200) observed after Wright-Giemsa staining of cells. The red asterisks, blue asterisks, and black arrows indicate enucleated erythroid cells at the terminal maturation stage, dead cells, and immature cells, respectively, and the remaining cells are orthochromatic erythroblasts. FIG. 17 shows the proportions of cells at different maturation stages under the conditions shown in FIG. 16. FIG. 18 shows the results obtained after culture of erythroid cells using porous structures made of different materials and having different pore sizes: the left images show pellets of mature erythroid cells collected after culture in the porous structures and the right images show cell viabilities.

DETAILED DESCRIPTION FOR CARRYING OUT THE INVENTION

The present invention will be explained in more detail with reference to the following examples. However, it will be obvious to those skilled in the art that these examples are provided for illustrative purposes only and are not to be construed as limiting the scope of the invention.

EXAMPLES

Experimental Methods

Example 1

Cell Culture and Enumeration

CD34+ cells were isolated from the cord blood of healthy donors by using the immunomagnetic microbead selection method and EasySep CD34 isolation kit (StemCell Technologies). Some of the CD34+ cells were used for culture immediately after isolation or were frozen and stored until use. The cells were cultured under stroma- and serum-free conditions for 17 days [3, 4].

Several cytokines were added to induce the CD34+ cells to differentiate and proliferate. From day 0 to day 7, the cells were cultured in media supplemented with 10 μM hydrocortisone (Sigma), 100 ng/ml stem cell factor (SCF; R&D Systems), 10 ng/ml interleukin (IL)-3 (R&D Systems), and 6 IU/ml erythropoietin (EPO; Calbiochem). From day 7 to day 13, basophilic erythroblasts were cultured in media supplemented with 50 ng/ml SCF, 10 ng/ml IL-3, and 3 IU/ml EPO. From day 13 to day 17, 2 IU/ml EPO was added [3, 4]. On day 17, when the proportions of polychromatic erythroblasts and orthochromatic erythroblasts reached ≥50%, 3D culture experiments were conducted for comparison. On day 17 of culture, 2 IU/ml EPO and 5% cord blood plasma derived serum were added for 3D culture [5].

The culture media were replenished every other day. The cells were cultured in a $CO_2$ incubator (Sanyo) at 37° C. and 5% $CO_2$. The numbers of variable cells were calculated by trypan blue staining. Cell integrity and maturation stage were analyzed by counting at least 400 cells per group in a blinded manner. The analysis was performed in a blinded manner by two investigators who were unaware of the cell culture conditions.

Example 2

Imaging of Erythroid Cells

Cells were plated on a slide using a cell centrifuge (Cellspin, Hanil Science Industrial) and subsequent Wright-Giemsa staining (Sigma-Aldrich). The stained cells were analyzed for maturation stage, myelodysplasia, and cell integrity.

Example 3

2D Plate Culture and 3D Packed Cell Culture

Figure 1:
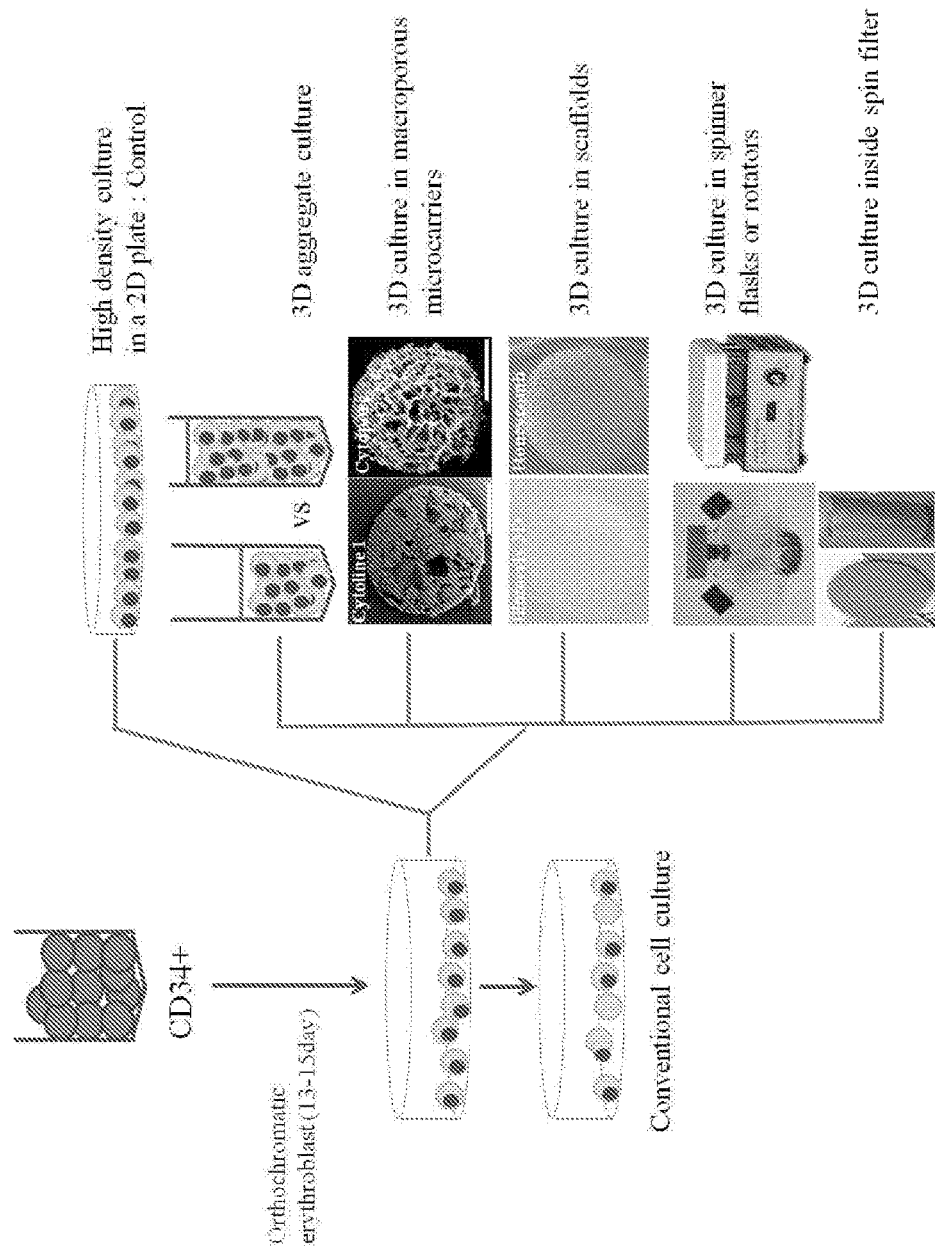
FIG. 1 shows 2D plate culture, 2D high density culture, packed cell culture of erythroid cells using macroporous microcarrier type Cytoline 1, packed cell culture of erythroid cells using Cytopore, packed cell culture of erythroid cells using Biomatrix 3D, packed cell culture of erythroid cells using Honeycomb, and spinner flasks, rotators, and a cylindrical spin filter for medium circulation conditions.

On days 15-17 of culture, the erythroid cells (polychromatic/orthochromatic erythroblasts) at the terminal maturation stage were divided and cultured under the conditions shown in FIG. 1. The control cells were cultured at a density of $1\times10^6$ cells/mL in a 6-well 2D plate. In the experimental groups, the cells were allowed to be packed at a density of $2\times10^7$ cells/mL in tubes and cultured in a state in which the tubes stood upright. Basal media used in the control and the experimental groups were supplemented with 5% plasma-derived serum [5]. After culture for 24 and 48 h, the cell numbers and viabilities were determined and the maturation stages of cells were confirmed using Wright-Giemsa staining.

Example 4

Determination of Stage for 3D Culture

In this example, an optimum maturation stage for packed cell culture of erythroblasts was determined. Packed cell culture started when 50% or more of the basophilic erythroblasts remained (on day 13 of culture) and the proportion of polychromatic/orthochromatic erythroblasts was 50% or more.

Example 5

2D Plate Culture and 3D Packed Cell Culture (100 μl, 200 μl)

As the cell number increases, it is difficult for nutrients to diffuse into cell packed portions or for toxic metabolites, such as $CO_2$ and lactate, to exit to the outside. In this example, an optimum packing scale upon packed cell culture of polychromatic/orthochromatic erythroblasts was confirmed. To this end, the yields and enucleation rates of erythrocytes under the respective conditions were compared. The control cells were cultured at a density of $1\times10^6$ cells/mL in a 6-well plate. In experimental group I, the cells were allowed to settle and packed at a density of $2\times10^7$ cells/mL in a conical tube and cultured. In experimental group II, the cells were cultured at a density of $2\times10^7$ cells/2 ml. The cell packing scale of experimental group II was twice in volume as large as that of experimental group I. The tubes had a size such that the cells of experimental groups I and II were sufficiently packed to create a 3D packing environment. The same culture solutions were used. After culture for 24 and 48 h, the cell numbers and viabilities were determined and the maturation stages of cells were confirmed using Wright-Giemsa staining.

Example 6

2D Culture and 3D Packed Cell Culture in Porous Structures

In this example, the packing scale of polychromatic/orthochromatic erythroblasts was increased to reproduce a 3-dimensional environment of the bony trabeculae. To this end, materials that are applicable to humans and have dimensions similar to the bony trabeculae space were selected and compared. The first material was Cytopore (GE healthcare) made of 100% cellulose, which was a porous carrier having an average pore size of 30 μm, a density of 1.03 g/ml, a particle diameter of 200-280 μm, an effective surface area of 1.1 $m^2$/g, and a volume of 40 ml/g. The second material was Cytoline (GE healthcare) made of polyethylene and silica and having a pore size of 1-400 μm, a density of 1.32 g/ml, a settling velocity of 120-220 cm/min, a length of 1.7-2.5 cm, a thickness of 0.4-1.1 cm, a surface area of 0.3 $m^2$/g or more, which were similar to those of the bony trabeculae space.

A control for the 3D experimental groups was the same as that for the 2D plate culture conditions. Cytopore was placed in a tube (experimental group I) and Cytoline 1 was placed in a tube (experimental group II) (see FIG. 4), polychromatic/orthochromatic erythroblasts were added thereto, and packed and cultured at a density of $1\times10^7$ cells/mi. Culture was continued until the terminal maturation stage was reached. After culture for 24 h and 48 h, the cell numbers and viabilities were determined and the maturation stages of cells were confirmed using Wright-Giemsa staining.

Example 7

3D Packing in Spinner Flasks

In this example, it was confirmed whether cells at the maturation stage were resistant to shear stress caused by a weak flow and were squashed in a 3D packing situation. Control cells were tested by the same procedure as above. For the experimental groups, cells were added at a density of $1.0\times10^7$ cells/ml to Cytoline 1 in spinner flasks and cultured. Generally, cells are immobilized in a packed bed bioreactor. In this example, erythroblasts, which are similar to adherent cells rather than to floating cells, are placed in the pores but some of them escape from the microcarriers by a media flow and float outside the microcarriers.

The fact that erythroblasts are very susceptible to shear stress caused by a flow of fluid was confirmed at various RPM conditions. Thus, after the rotating velocity of a bioreactor was adjusted to RPM 25 to minimize the influence of shear stress, cells were cultured until the terminal maturation stage was reached. RPM 25 is the lowest rotating velocity of the bioreactor. The numbers of viable cells in the control and the experimental groups were calculated by trypan blue staining and the maturation stages of cells were analyzed using Wright-Giemsa staining every 24 h.

Example 8

3D Packing Using Cytopore and Cytoline 1 in Spinner Flasks

For scale-up culture considering the bone marrow situation, conditions for optimum medium exchange without cell squash despite packing of large volume and quantity of cells were investigated. To this end, Cytopore or Cytoline 1 was added to a spinner flask and cultured. The same conditions were used for a control. Experimental groups were cultured at a density of $1\times10^7$ cells/ml in the spinner flasks. The maturation stages of cells were analyzed using Wright-Giemsa staining every 24 h.

Example 9

3D Culture Using Cytoline 1 in Spin Filter in Spinner Flask (Medium Exchange)

Cytoline 1 was selected as a porous structure for 3D packed cell culture because it was more suitable for the reproduction of an in vitro bone marrow environment. It was found that non-adherent erythroid cells are not immobilized in the porous microcarrier and some of them escape from the carrier and float in the form of suspension. In this case, erythroid cells do not come into contact with each other. In this example, erythroid cells were packed and grown in the pores and they, together with the carrier, were trapped in a cylindrical spin filter for easy medium exchange and immobilized and cultured in an incubator. Generally, erythroid cells belonging to the smallest cell types easily escape through an 8 μm filter from a bioreactor due to the large pore diameter of the filter. Thus, in this example, erythroid cells were trapped in a small spin filter whose mesh size was 3 μm and were cultured while allowing for slow exchange of culture solution. The same control was used as above. In experimental group I, cells were trapped and cultured at a density of $1\times10^7$ cells/ml in Cytoline 1 in a stationary state (at RPM 0). In experimental group II, cells were cultured while shaking at RPM 25. The maturation stages of the cells of the control and the experimental groups were analyzed every 24 h.

Example 10

2D High Density Culture and 3D Packed Cell Culture Using Cytoline 1

From the above experimental results, it was concluded that 3D packed cell culture was more advantageous in cell viability and cell maturation than 20 plate culture. The use of the porous structure lowered the cell viability for 3D packed cell culture but led to a marked increase in cell maturation. These results can be explained by the reproduction of an in vitro bone marrow environment and can be considered innovative for the production of erythroid cells at the terminal maturation stage at a high density.

The present inventors have reported previously that when cells are cultured at a higher density than a general cell density such that they come into contact with each other on the bottom of a 2D plate, high cell viability and better cell maturation are obtained. The present inventors have conducted comparative experiments whether 3D culture produced a larger quantity of erythrocytes than 2D high density plate culture due to the higher frequency of contact and packing interfered with medium exchange. The same culture solution was used. Control cells were cultured at a density of $1 \times 10^6$ cells/mL in a 24-well 2D plate. In experimental group 1, cells were cultured at a density of $1 \times 10^7$ cells/mL with Cytoline 1 in the tube. In experimental group II, cells were cultured at a density of $1 \times 10^7$ cells/ml with Cytoline 1 in the spin filter. The numbers of viable cells in the control and the experimental groups were determined by trypan blue staining and the maturation stages of cells were analyzed using Wright-Giemsa staining every 24 h.

Example 11

Additional Experiment for Selection of Suitable Porous Structure

Erythroid cells at the terminal maturation stage were subjected to packed cell culture at high densities on macroporous microcarriers and scaffolds as 3D porous structures to confirm the effect of the 3D porous structures on the culture of the erythroid cells. 3D porous structures should have a number of pores to stimulate the interactions of cells, reproduce the porosity of the in vivo bony trabeculae, and made of biocompatible materials without damage to cells. To screen suitable porous structures, various pore sizes, skeletal shapes, and constituent components were applied as shown in Table 1. Control cells were cultured at a density of $1 \times 10^6$ cells/mL on a 6-well 2D plate.

TABLE 1

| Type | Material | Pore size (μm) | Diameter (mm) | Density (g/ml) |
|---|---|---|---|---|
| Macroporous microcarriers | Cytopore | 100% cellulose matrix | 30 | 0.2-0.28 | 1.03 |
| | Cytoline 1 | Polyethylene, silica | 10-400 | 1.7-2.5 | 1.3 |
| Scaffolds | Honeycomb | 100% bovine collagen | 200-400 | 6 (diameter) × 2 (height) | |
| | Biomerix 3D | Biostable polyurethane | 250-500 | 5 (diameter) × 2 (height) | |

Erythroid cells at the maturation stage were cultured at a density of $1 \times 10^7$ cells/mL in each porous structure in a spin filter for 3 days. Half of the whole medium was replaced with the fresh one daily and the cell morphology was confirmed by Wright-Giemsa staining.

Example 12

Measurement of the Ability of Cultured Cells to Transport Oxygen

Oxygen equilibrium curves of erythrocytes produced by packed cell culture in 3D scaffolds were measured using a Hemox analyzer (TCS Scientific) and were compared with those of peripheral blood of a healthy subject as a control.

Example 13

Additional Experiment for Selection of Structure for 3D Culture of Erythroid Cells In this example, a pore size and a material suitable for culture of erythroid cells were determined. To this end, cell packing experiments were conducted using various 3D structures. To select a material having a pore size of 500 μm or less for reproducing an intracellular skeletal structure and sufficient strength to support the constituents of bone marrow and a structure capable of easily collecting cells after culture, experiments were conducted on a 3D-printed scaffold, a microcarrier, a non-porous disk, and metal materials (Ni and stainless steel). The cell densities of a control and experimental groups and the conditions of culture media were the same as the above experimental conditions. Table 2 shows the specifications of the 3D structures.

TABLE 2

| Type | | Component | Pore size (μm) | Diameter (diameter × height) |
|---|---|---|---|---|
| 3D printed scaffold | 3D printed scaffold | Polycaprolactone | 500 | 8 mm × 2 mm |
| Microcarrier disk | Fibracel-microcarrier disk | Polyester mesh having polypropylene support | — | 6 mm × 0.1 mm |
| Metal structures | Nickel structure | Nickel | ~500 | 8 mm × 1.5 mm |
| | Stainless steel structure | Metal alloy | ~500 | 8 mm × 1.5 mm |

Example 14

Identification of Effect of Co-culture with Constituents of Bone Marrow

Actual erythroid islands in bone marrow were reproduced by co-culture of constituents of bone marrow and erythroid cells in 3D structures that mimic the bony trabeculae space where the hematopoietic process occurs actively. The maturation of cells are promoted in the erythroid islands. Mesenchymal stem cells (MSCs), osteoblasts, and mature erythroid cells were co-cultured for 192 h while maintaining their ratio constant (2:1:10). The results were compared to those obtained in 2D plate culture. A mixture of stem line II and Dulbecco Modified Eagle Medium low glucose media in a ratio of 9:1 was used as a basal medium suitable for co-culture of the three kinds of cells. Only a portion of the whole medium was replaced with the fresh one daily. Thereafter, populations of cells (CD45 for myeloid cells, CD71 for erythroid cells, and CD51 and CD90 for MSCs) were confirmed by flow cytometry. Various experiments were conducted to establish optimum culture conditions. To this end, the constituent cells were cultured simultaneously. Alternatively, MSCs and osteoblasts were first cultured and were co-cultured with erythroid cells 3 h later.

Experimental Results

1. Packing Effect of Basophilic/polychromatic Erythroblasts (2D Plate Culture and 3D Packed Cell Culture)

Figure 2:
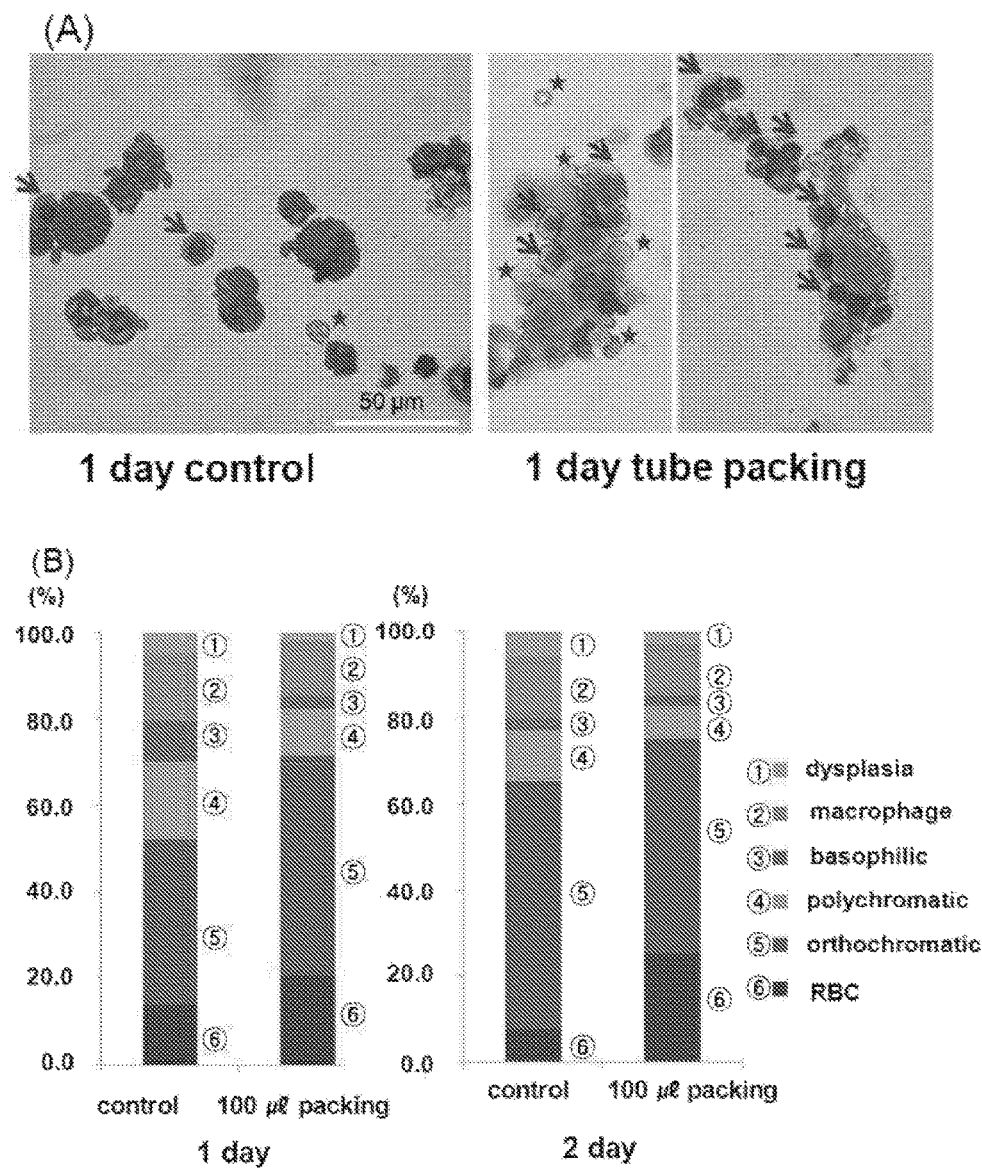
FIG. 2 shows (A) images (×200) observed after 2D plate culture and 3D packed cell culture of polychromatophilic erythroblasts/orthochromatic erythroblasts for 1 and 2 days and Wright-Giemsa staining: the asterisks indicate enucleated erythroid cells at the terminal maturation stage and the arrows indicate orthochromatic erythroblasts; and (B) compares the proportions of cells at different maturation stages and the yields of erythrocytes under the conditions shown in (A).

Hematopoietic stem cells isolated from cord blood were differentiated in a culture medium for 13-17 days. The cells were packed at a high density when the proportions of basophilic/polychromatic erythroblasts reached ≥50%. Control cells were cultured in a plate. In the experimental group, cells were packed at a density of $2 \times 10^7$ cells/ml in tubes. On days 1 and 2 of culture, the maturation stage and viability of erythroid cells were observed (see FIG. 2A). Unlike in 2D plate culture, erythroid cells were cultured while keeping their intimate contact with each other in 3D tubes, similarly to erythroid islands in bone marrow (see FIG. 2A). After days 1 and 2 of culture, the proportions of orthochromatic erythroblasts in the control were 38.5% and 57.8%, respectively. In contrast, the proportions of orthochromatic erythroblasts in the experimental group having undergone 3D packing were 50.9% and 49.6% (see FIG. 2B). the numbers of enucleated erythrocytes (20.6% and 25.2%) in the experimental group were increased after 3D packed cell culture than in the control (13.7% and 7.5%). On day 2 of culture, the proportions of orthochromatic erythroblasts in the experimental group were smaller than those in the control, which appears to be because more orthochromatic erythroblasts were enucleated into erythrocytes in the experimental group. Myelodysplasia were decreased in the control (5.1% and 6.1%) and the experimental group (2.3% and 3.1%) on days 1 and 2 of culture. Myelodysplasia is a disorder that occurs when nuclei are not sufficiently divided and are split or several nuclei remain in one cytoplasm because of a bad culture environment. Therefore, it can be concluded that the 3D packed cell culture environment is more suitable for cell maturation and erythrocyte production.

2. Packing Scale of Orthochromatic Erythroblasts

Figure 3:
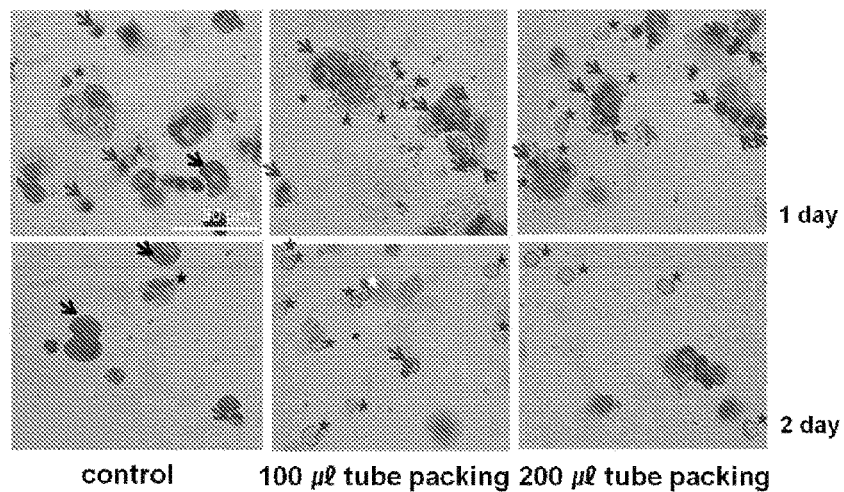
FIG. 3 shows the results obtained after 2D plate of orthochromatic erythroblasts and 3D high density packed cell culture of orthochromatic erythroblasts at different densities for 1 and 2 days: (A) shows the results (×200) of Wright-Giemsa staining on orthochromatic erythroblasts, the red asterisks, blue arrows, black arrows, white asterisks, and block asterisks indicate enucleated erythroid cells at the terminal maturation stage, orthochromatic erythroblasts, myeloid cells, cells undergoing enucleation, and cells with dysplasia, respectively; and (B) compares the proportions of cells at different maturation stages and the yields of erythrocytes under the conditions shown in (A).
Figure 3:
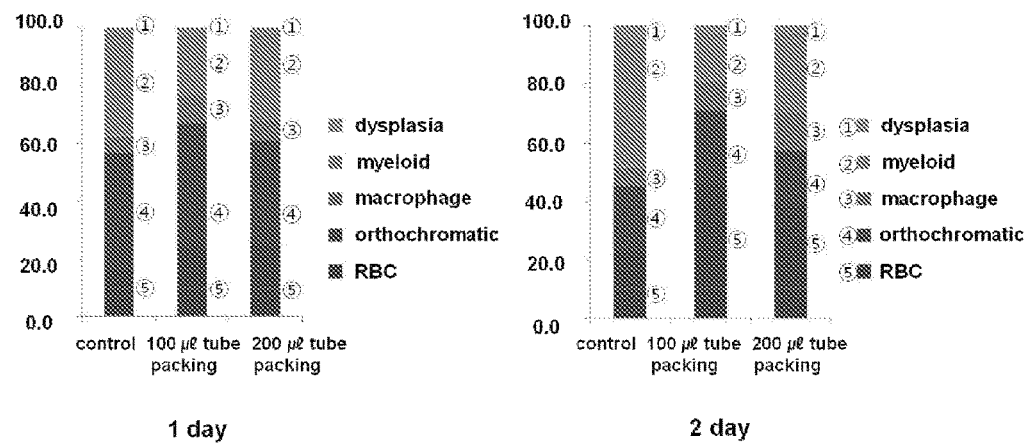

In the above experiments, 3D high density packing cell culture was confirmed to be more effective in cell maturation than 2D plate cell culture because it reproduced the in vivo bone marrow environment where intercellular contact increases. To find an optimum cell packing scale for 3D high density packed cell culture, erythroblasts at the maturation stage in experimental groups I and II were compared with those in the 2D plate culture control. In experimental group I, cells were subjected to packed cell culture at a density of $1 \times 10^7$ cells/ml in a narrow tube where a 3D packing environment could be created. In experimental group II, cells were subjected to packed cell culture at a density of $2 \times 10^7$ cells/ml. After days 1 and 2 of culture, the proportions of orthochromatic erythroblasts were 40.7% and 22.6% for the control, 43.3% and 23.1% for experimental group I, and 36.0% and 18.2% for experimental group II, respectively. These results demonstrate that the conditions of experimental group I are more effective for cell maturation upon 3D packed cell culture (see (A) and (B) of FIG. 3). Due to the enucleation effect, the proportions of erythroid cells at the terminal maturation stage were higher in experimental group I (23.8% and 46.1%) and experimental group II (23.0%, 30.1%) than in the control (16.1% and 22.6%) on days 1 and 2 of culture. These results are explained by an increase in the number of enucleated erythrocytes upon packing in experimental groups I and II. The packing effect was observed to be more significant in experimental group I than in experimental group II. On day 2, myelodysplasia was decreased to 3.8%, 2.7%, and 2.6% upon packing for the control and experimental groups I and II, respectively. On day 1, cell viability was increased by 4.6% and 5.4% in experimental groups I and II, respectively, compared to in the control. On day 2, cell viability was increased by 45.7% and 5.9% in experimental groups I and II, respectively, compared to in the control (see FIG. 3B).

3. 3D Packed Cell Culture in Porous Structures

Cells at the maturation stage were cultured in an in vitro bony trabeculae environment. To this end, erythroblasts at the maturation stage cultured in the control were compared with those cultured in Cytopore and Cytoline I (see FIG. 4).

Figure 4:
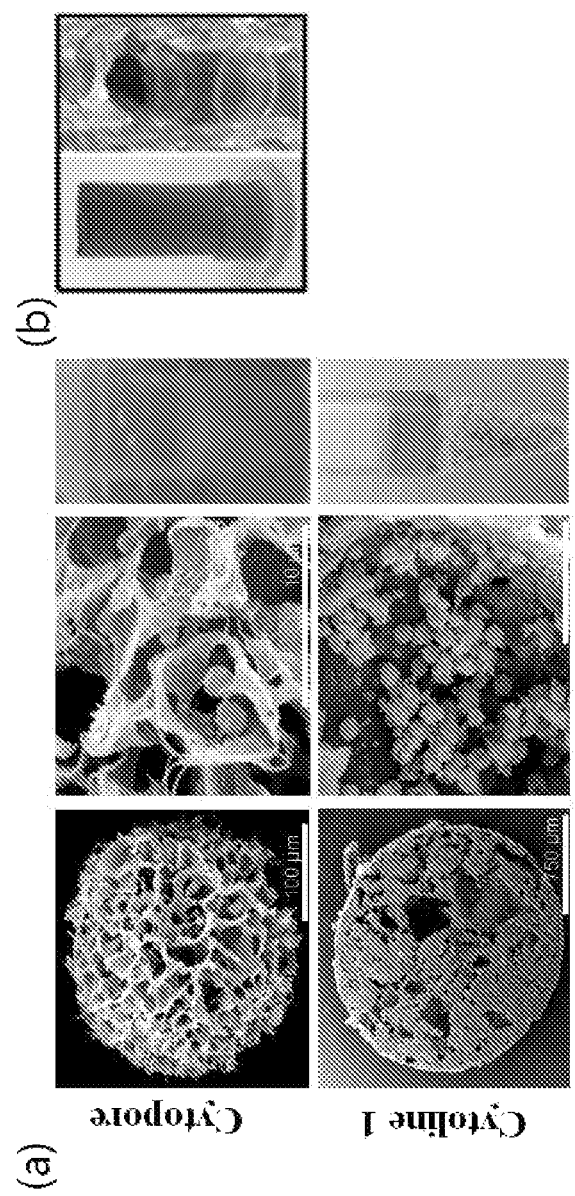
FIG. 4 shows (a) SEM images of Cytopore and Cytoline 1 as porous microcarriers (left), cell cultures (middle) in the microcarriers, and cell cultures in tubes (right) (the diameter of the upper wider portion was 6.5 mm; and (b) a cylindrical spin filter (left) (diameter 6.5 mm, height 15 mm) and erythroid cells grown at a density of $10^7$ cells/ml medium in a 12-well plate.
Figure 5:
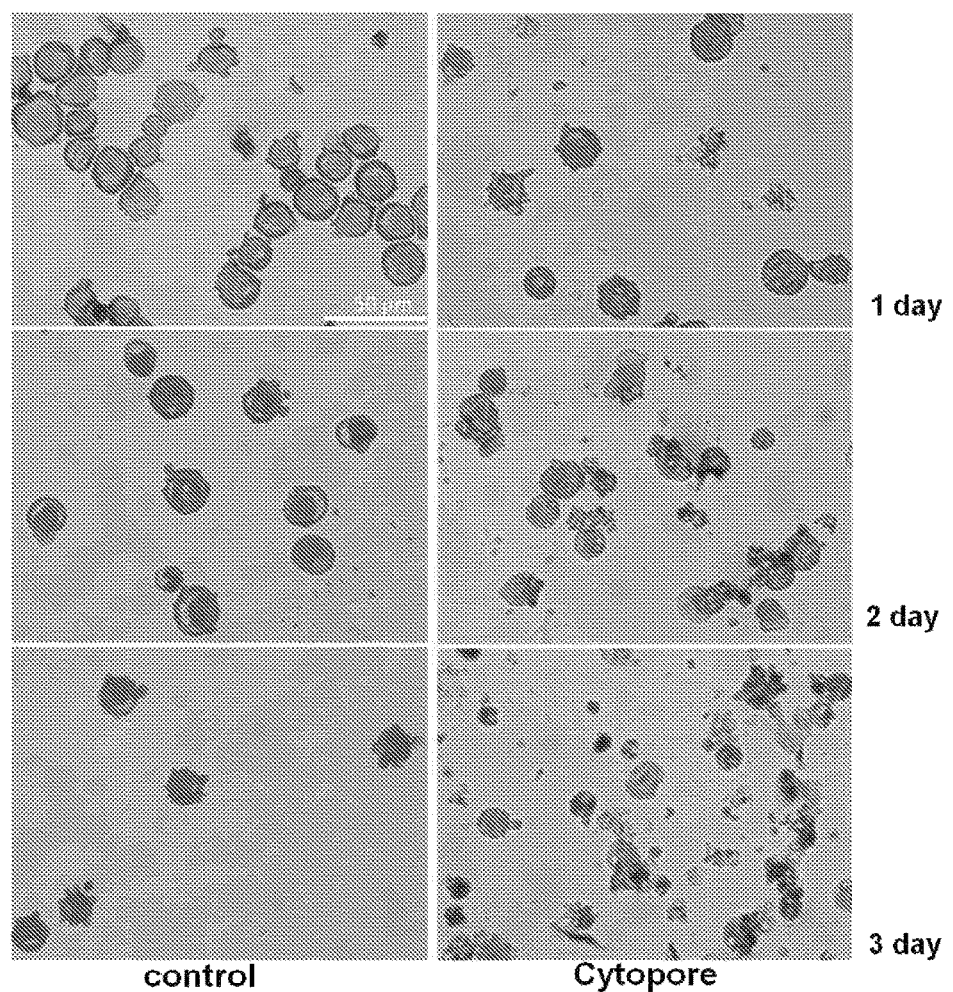
FIG. 5 shows viable erythroid cells on days 1, 2, and 3 of culture in Cytopore.

On days 1, 2, and 3 of culture, the viabilities of erythroid cells in Cytopore were lower than those in the control. This is thought to be because the spaces of the pores were too small to induce cell contact and medium circulation, as shown in FIG. 4 (see FIG. 5).

Figure 6:
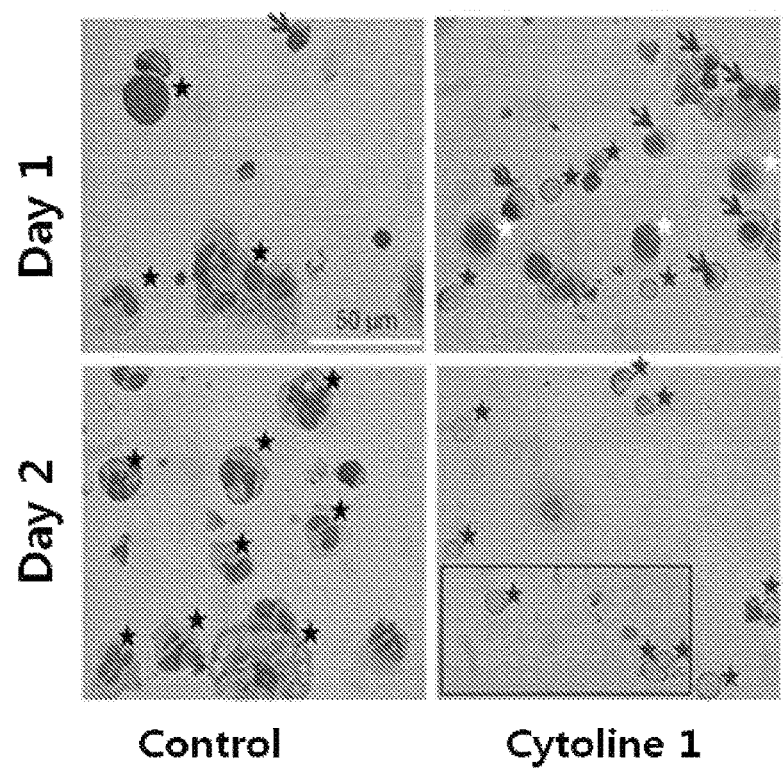
FIG. 6 shows viable cells after packed cell culture in Cytoline 1.
Figure 7:
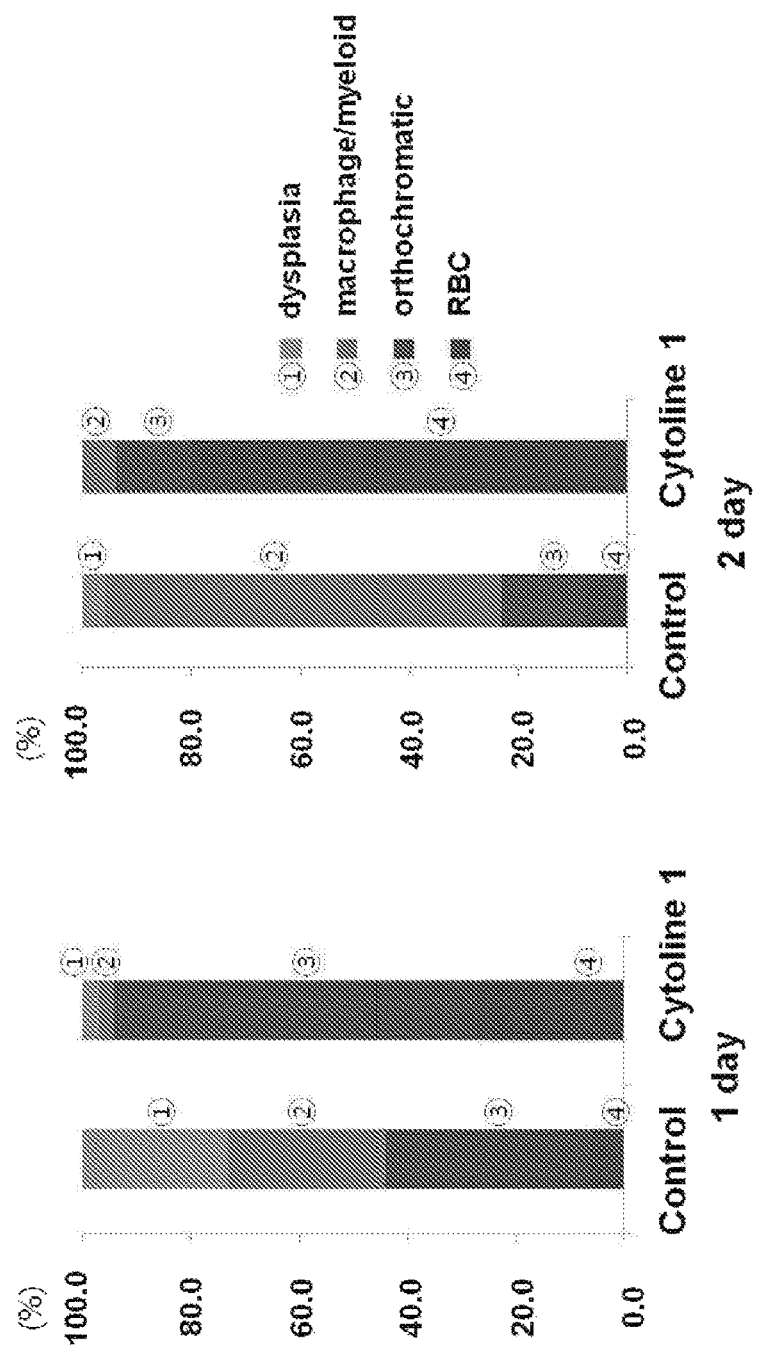
FIG. 7 shows the proportions of cells at different maturation stages after culture in Cytoline 1 for 1 and 2 days.
Figure 8:
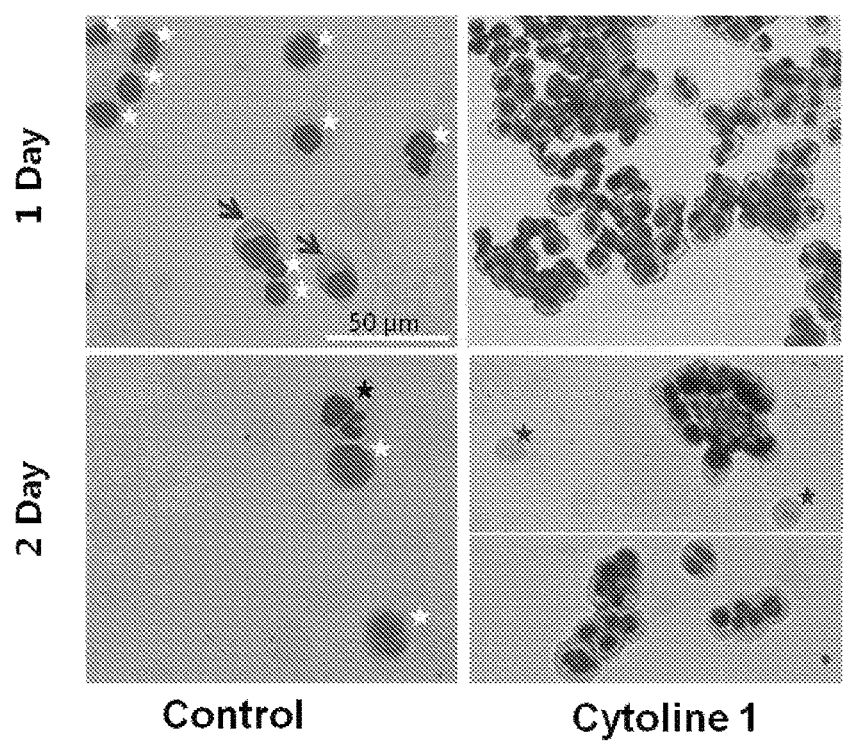
FIGS. 8 and 9 show the results observed after packing culture of cells of Case 2 derived from another cord blood for 1 day. Specifically.
Figure 9:
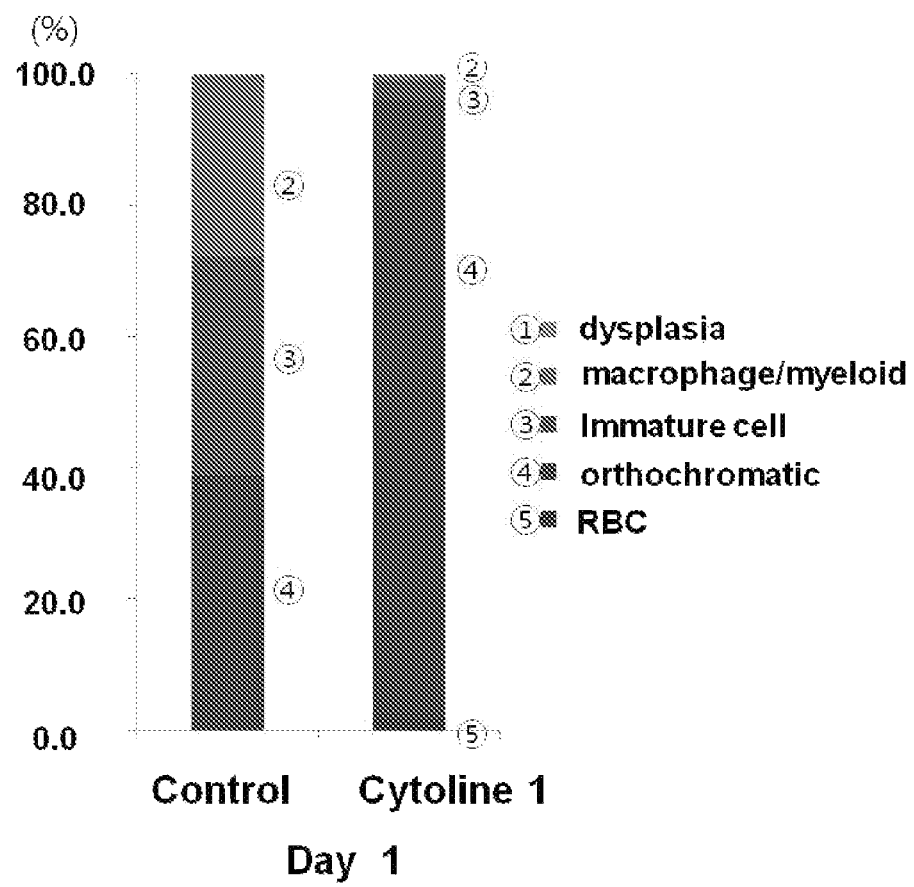

For Cytoline 1, cell maturation was efficient upon packed cell culture (see FIG. 6). As a result, the proportions of orthochromatic erythroblasts in the control were 38.3% and 15.6% and those of Case 1 of Cytoline 1 were 67.5% and 14.1% after days 1 and 2 of culture, respectively. The proportions of enucleated erythrocytes in Cases 1 and 2 of Cytoline 1 were much higher (26.9% and 80.0%) upon packing than those in the control (6.1% and 7.2%). Myelodysplasia was decreased in the control (26.9% and 4.0%) and Cytoline 1 (2.8% and 0.0%) (see FIG. 7). Cells of Case 2 derived from another cord blood was compared after packing for 1 day. The proportions of orthochromatic erythroblasts were 39% for the control and 94.1% for experimental group II. The higher proportion of orthochromatic erythroblasts in experimental group II indicates greatly increased cell maturation. Upon 3D packed cell culture in the presence of Cytoline 1, intercellular contact was increased and cells were matured more effectively (see FIGS. 8 and 9). Since live cells in the control were not erythroid cells but cells of other families, the viability of cells in the control were not compared.

4. Comparison of Culture of Erythroblasts in Spinner Flasks without Pores

Figure 10:
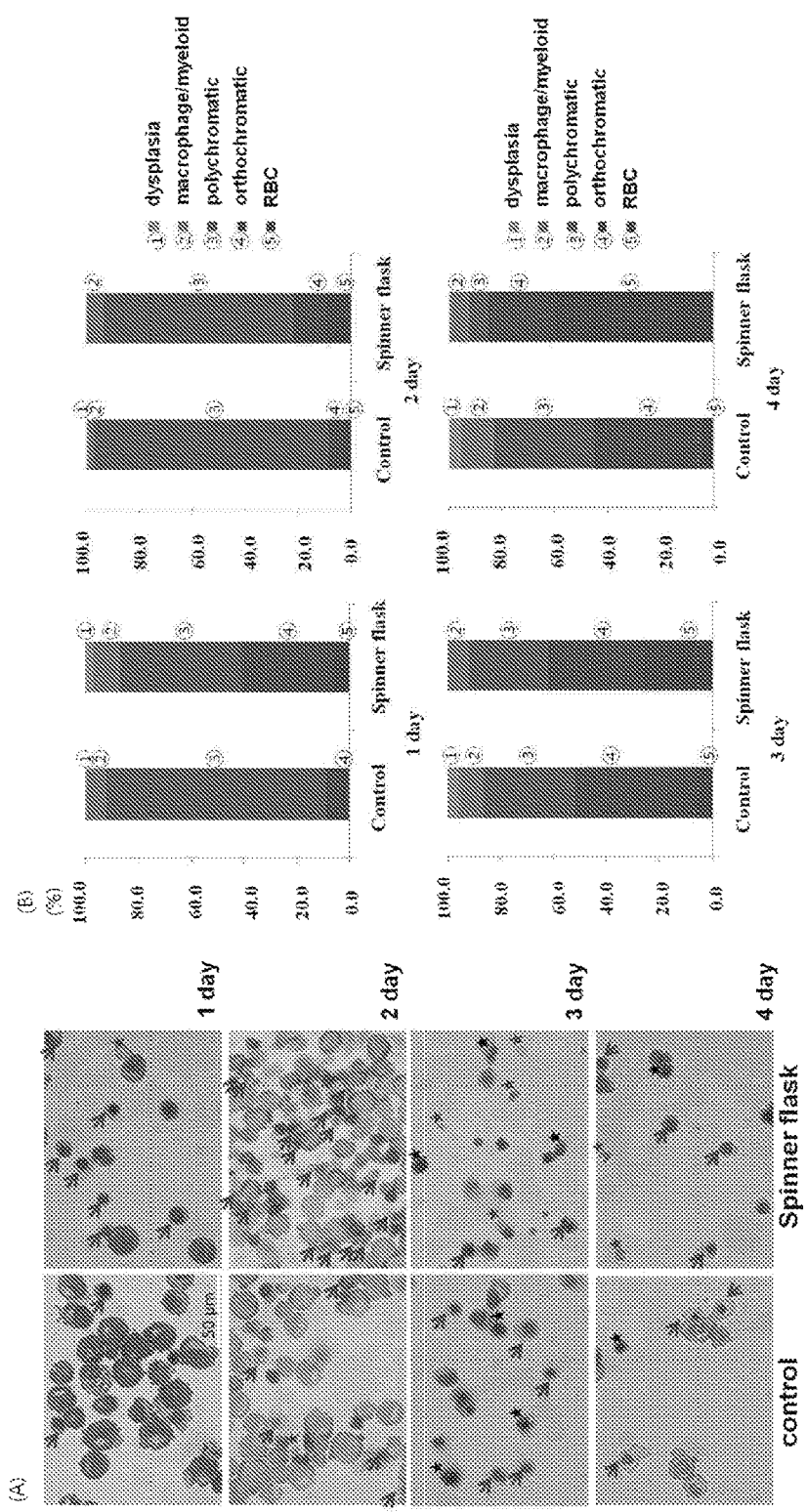
FIG. 10 shows (A) images obtained after erythroblasts was allowed to settle in a spinner flask and cultured without a microcarrier while rotating at RPM 25 and images obtained after 2D plate culture of erythroblasts; and shows (B) the proportions of cells at different maturation stages with increasing culture time.

In this example, it was confirmed whether polychromatic/orthochromatic erythroblasts at the maturation stage were resistant to shear stress (hydromechanical damage) caused by a weak flow in spinner flasks (see FIG. 10A). Cells were cultured with stirring at RPM 25, where shear stress was minimized, for 4 days. At this rate, cells were settled down at the bottom without floating. The proportions of orthochromatic erythroblasts in the control (9.1%, 5.9%, 46.2%, and 41.6%) and in experimental group I (35.0%, 12.8%, 36.0%, and 12.8%) were observed every 24 h (see FIG. 10B). The yields of erythrocytes were higher in experimental group I using a spinner flask (6.5%, 9.0%, 26.0%, and 59.3%) than in the control (0.0%, 2.7%, 5.8%, and 3.4%), Therefore, culture in the presence of Cytoline 1 in the spinner flask was also effective in cell maturation and erythrocyte production. However, the cell viability of orthochromatic erythroblasts was lower and the morphology of erythrocytes was not well maintained by shear stress in experimental group I compared to in the control. Therefore, pores protected from shear stress are suitable for culture (see FIG. 10A).

5. Culture in the Presence of Cytopore in Spinner Flasks

Figure 11:
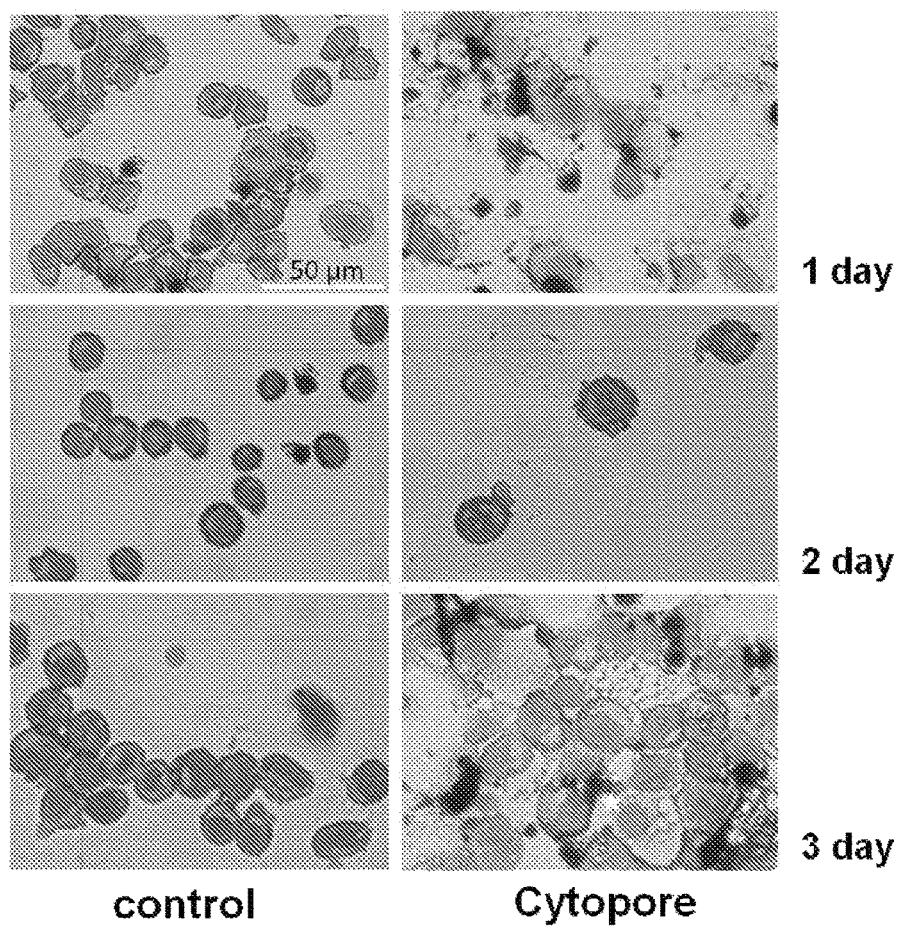
FIG. 11 shows the results obtained after culture of cells using Cytopore in a spinner flask.

To reduce cell squash and shear stress in large volume, Cytopore and Cytoline 1 were added and cultured in separate spinner flasks for 3D packed cell culture. For Cytopore, the number of mature erythroid cells did not increase even in the spinner flask, as in the results obtained in the previous experiment. Therefore, Cytopore was confirmed to be unsuitable for culture of erythroid cells (see FIG. 11).

6. Culture in the Presence of Cytoline 1 in Spinner Flask

Figure 12:
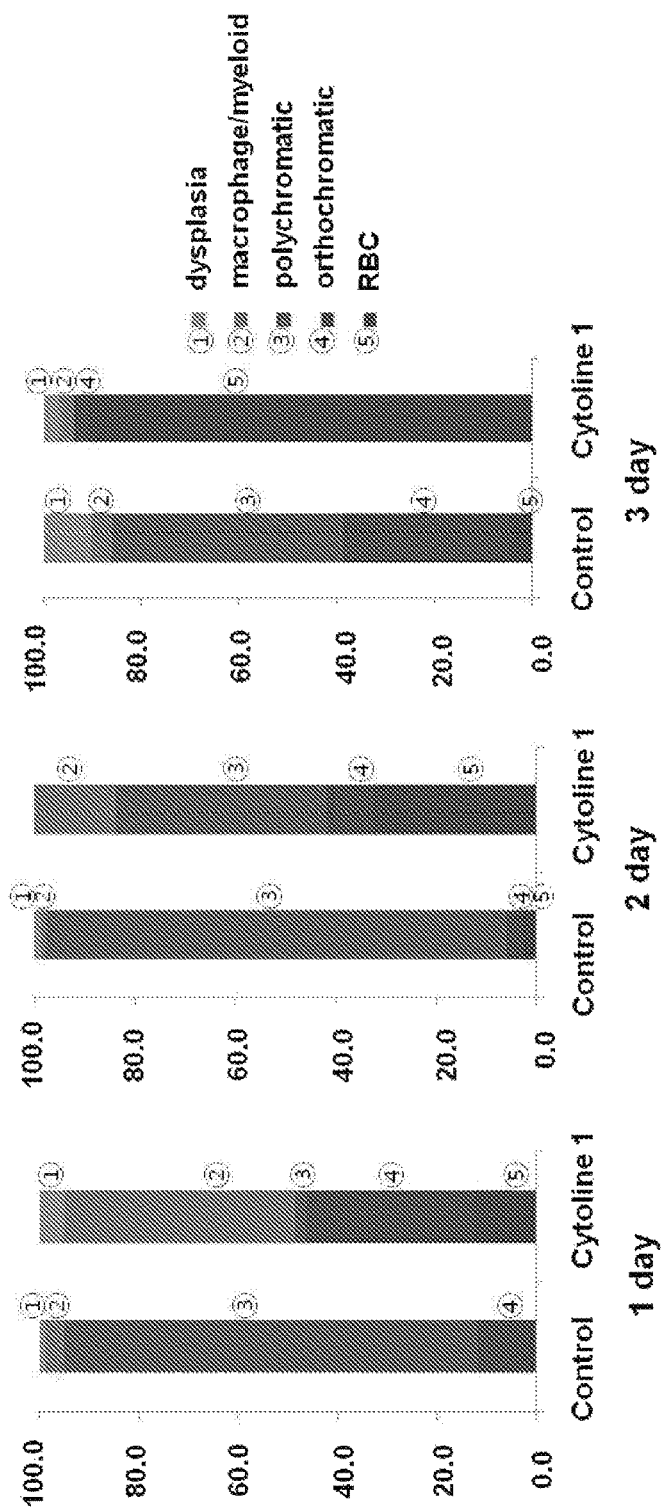
FIG. 12 compares the proportions of cells at different maturation stages after 3D culture using Cytoline 1 in a spinner flask.

The proportions of orthochromatic erythroblasts were 11.8%, 3.9%, and 34.7% in the control and 34.1%, 9.7%, and 3.1% in the experimental group. When Cytoline 1 was added and cultured in a spinner flask for 3D packed cell culture, intercellular contact was increased and cells were matured more effectively (see FIG. 12). Due to the enucleation effect, the proportions of enucleated erythrocytes were higher in the experimental group (12.2%, 32.3%, and 90.6%) than in the control (0%, 2.3% and 4.2%) on days 1, 2, and 3 of culture. Therefore, it can be concluded that since cells at the maturation stage in Cytoline 1 are less susceptible to sheer flow while maintaining their packing effect, the presence of Cytoline 1 is effective for the production of erythroid cells at the terminal stage.

Figure 13:
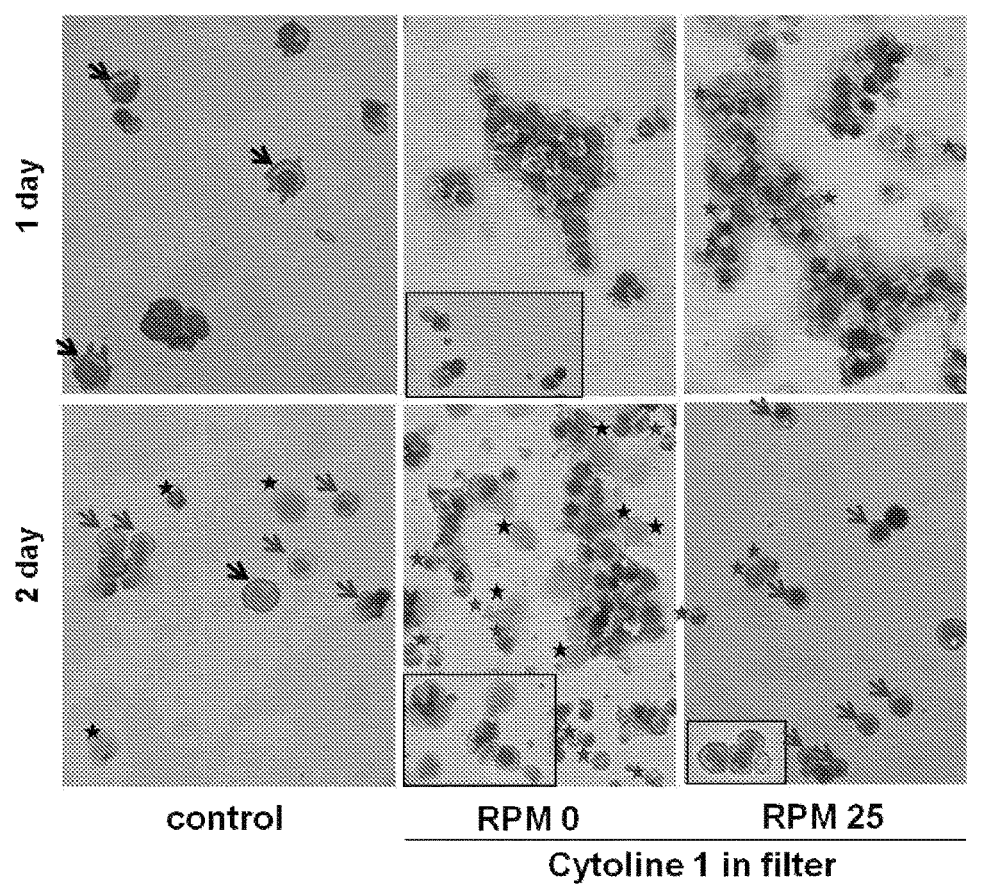
Figure 14:
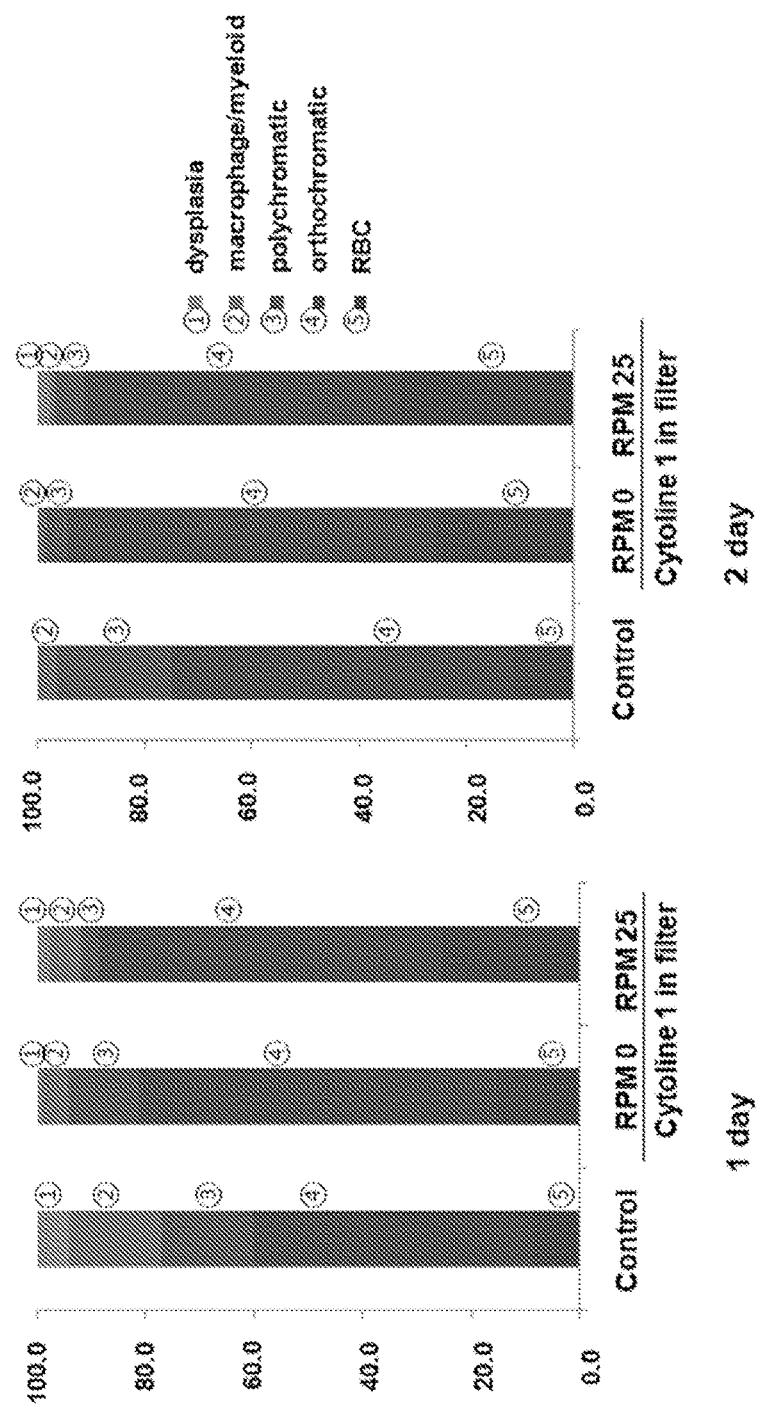
FIG. 14 shows the proportions of cells at different maturation stages under the conditions shown in FIG. 13.
Figure 15:
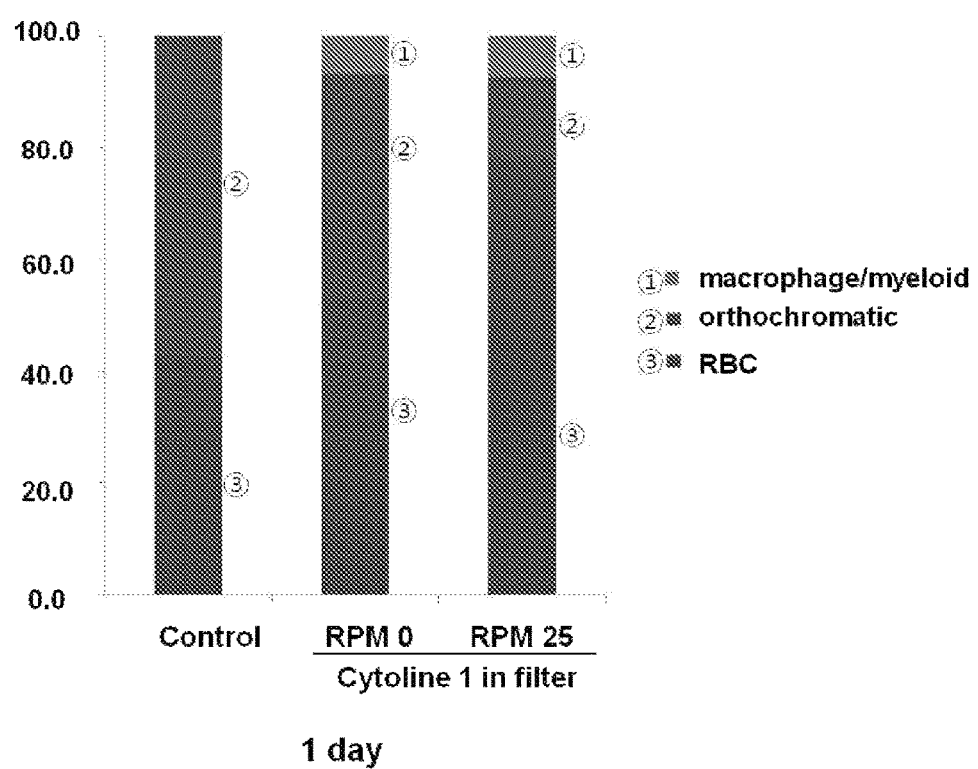
FIG. 15 compares the yields of erythrocytes from cells of a cord blood derived case different from that shown in FIG. 13.

7. Comparison of Effect of Spin Filter and Cytoline 1 in Spinner Flask and Shaking RPM on 3D Culture To prevent cells from escaping from the microcarriers and from receiving shear stress caused by a medium flow without being packed, microcarriers and cells were trapped in a spin filter (3 μm) to allow for slow exchange of culture solution while maintaining the packing effect of cells unchanged. In experimental group I, cells were trapped in a spin filter and cultured with Cytoline 1. Considering shear stress, cells were stirred at RPM 0. In experimental group II, cells were cultured with shaking at RPM 25 for better medium exchange. After days 1 and 2 of culture, the proportions of orthochromatic erythroblasts were 51.4% and 64.2% in the control, 66.4% and 70.0% experimental group I, and 63.2% and 59.4% experimental group II. The numbers of enucleated erythrocytes were 15.0% and 25.6% in experimental group I and 25.5% and 32.3% experimental group II, which were larger than that in the control (8.6% and 10.7%). Particularly, larger numbers of enucleated erythrocytes were observed in experimental group II. On day 1 of culture, less myelodysplasia was observed in experimental groups I and II (5.7%, 1.0%, and 2.0%) than in the control (FIGS. 13-15). No cell debris was observed in the spin filter. That is, the use of the porous structure maintained the packing effect of cells, and the use of the spin filter reduced shear stress caused by a medium flow and allowed easy culture solution exchange. Therefore, the combination of the porous structure and the spin filter is the most effective for the maturation of cells and the production of erythroid cells.

8. 2D High Density Culture and 3D Packed Cell Culture Using Cytoline 1

Figure 16:
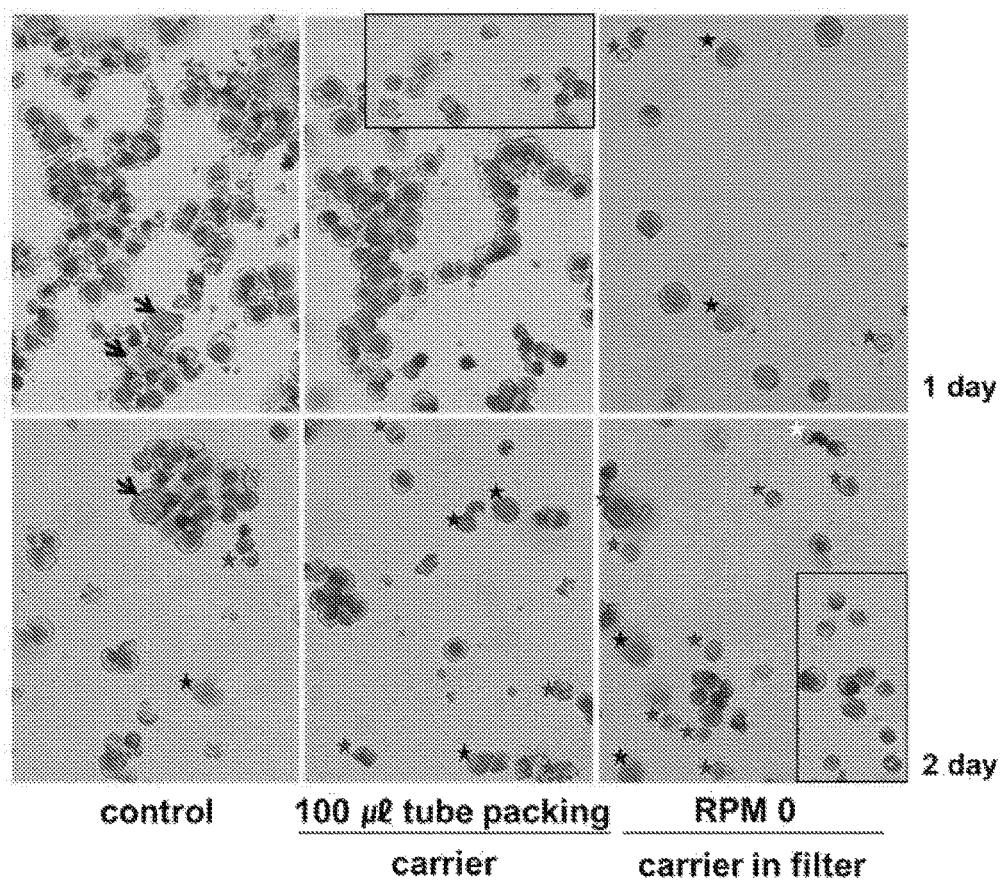
FIGS. 16 to 18 show the results observed after 2D high density culture and 3D high density packed cell culture of erythroid cells. Specifically.
Figure 17:
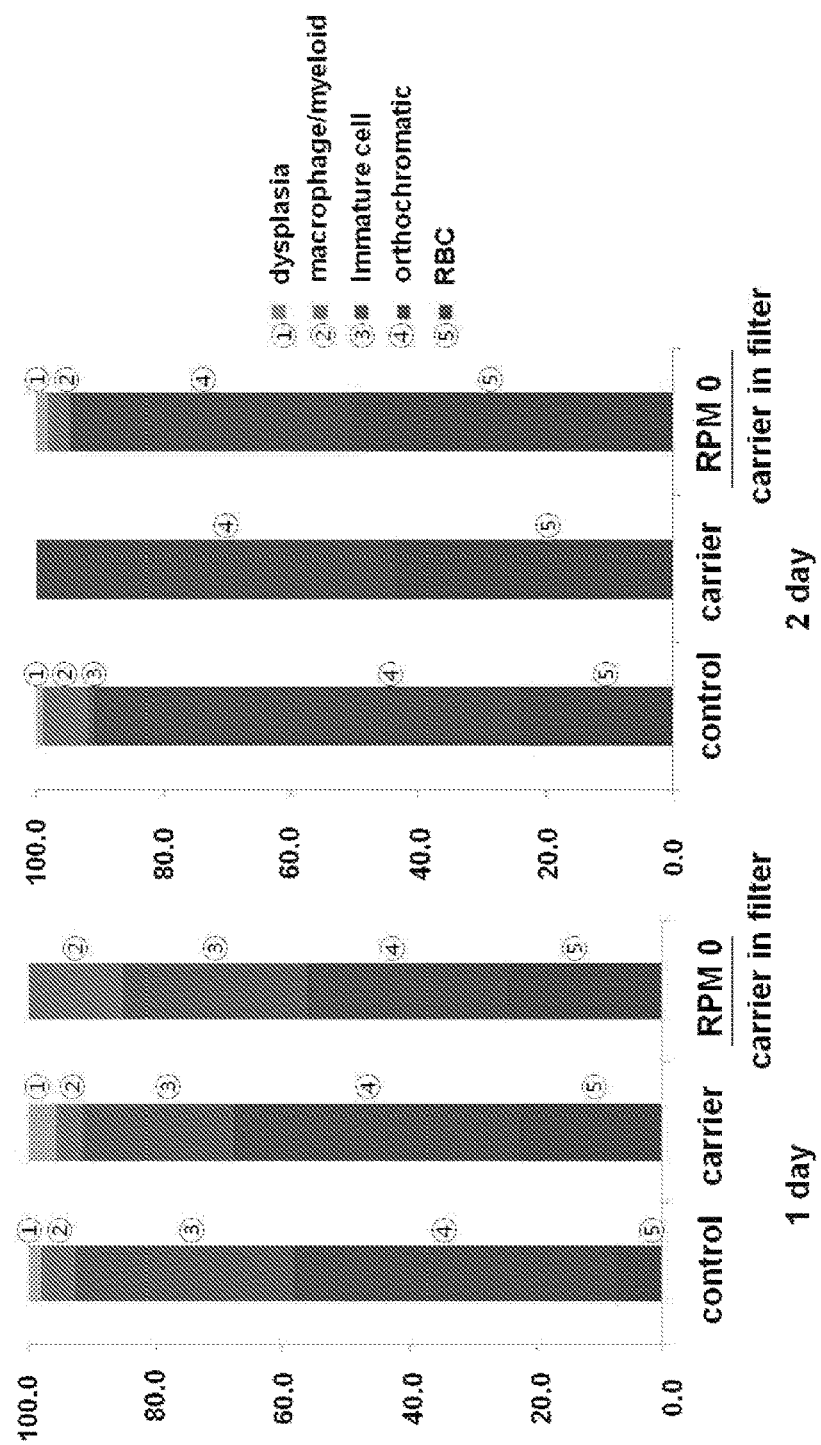
Figure 18:
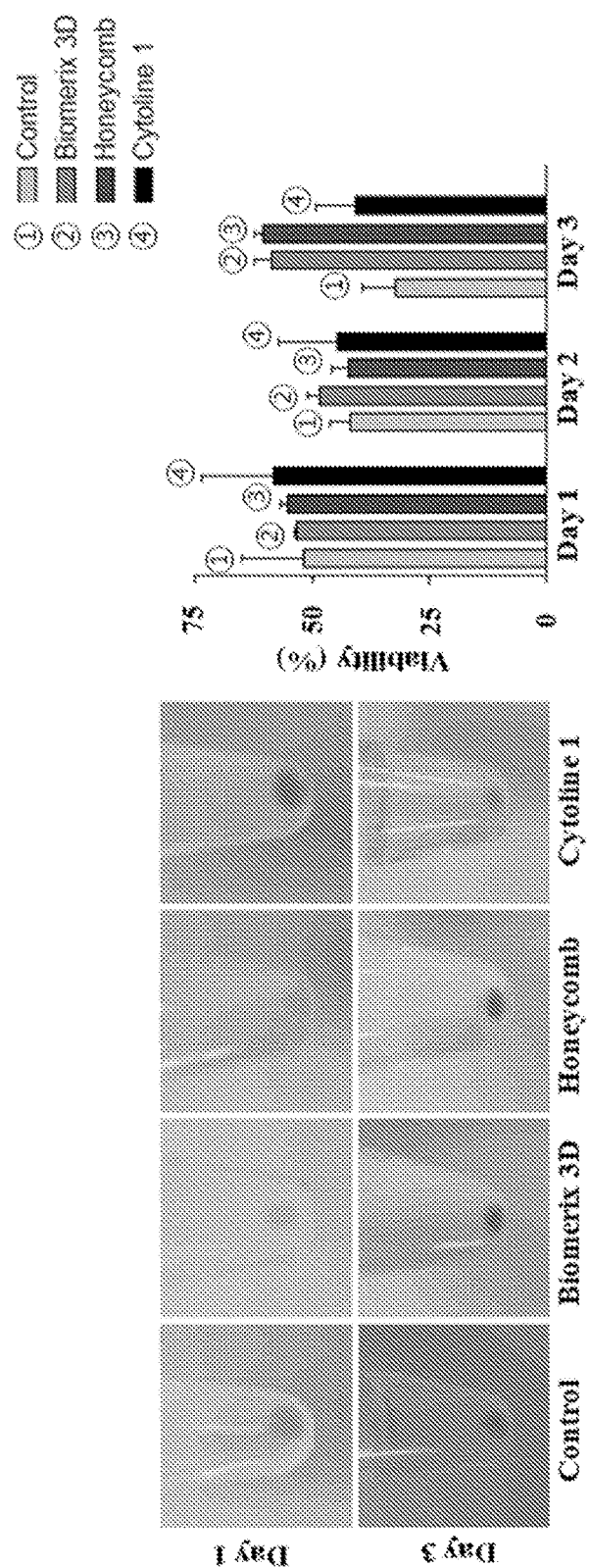

To again demonstrate the above experimental results, the present inventors reproduced the experiments with better results. Control cells were cultured at a high density on a 2D plate, cells of experimental group I were subjected to 3D packed cell culture in the presence of Cytoline 1 in a tube, and cells of experimental group II was subjected to 3D packed cell culture with Cytoline 1 in a spin filter. After days 1 and 2 of culture, the proportions of orthochromatic erythroblasts were 60.0% and 66.7% in the control, 45.1% and 56.5% in experimental group I, and 31.7% and 44.3% in experimental group II, respectively. The conditions of the experimental groups were confirmed to be more effective in cell maturation upon 3D packed cell culture (FIGS. 16-18). Due to the enucleation effect, the proportions of enucleated erythrocytes were higher in experimental group I (22.5% and 43.5%) and experimental group II (24.4% and 50.4%) than in the control (7.2% and 24.2%). In the experimental groups, intercellular contact was increased, contributing to effective packing. Myelodysplasia was decreased in the control (2.0% and 1.0%), experimental group I (4.2% and 0.0%), and experimental group II (0.0% and 1.7%) (see FIGS. 16-18).

9. Selection of Porous Structure

Figure 19:
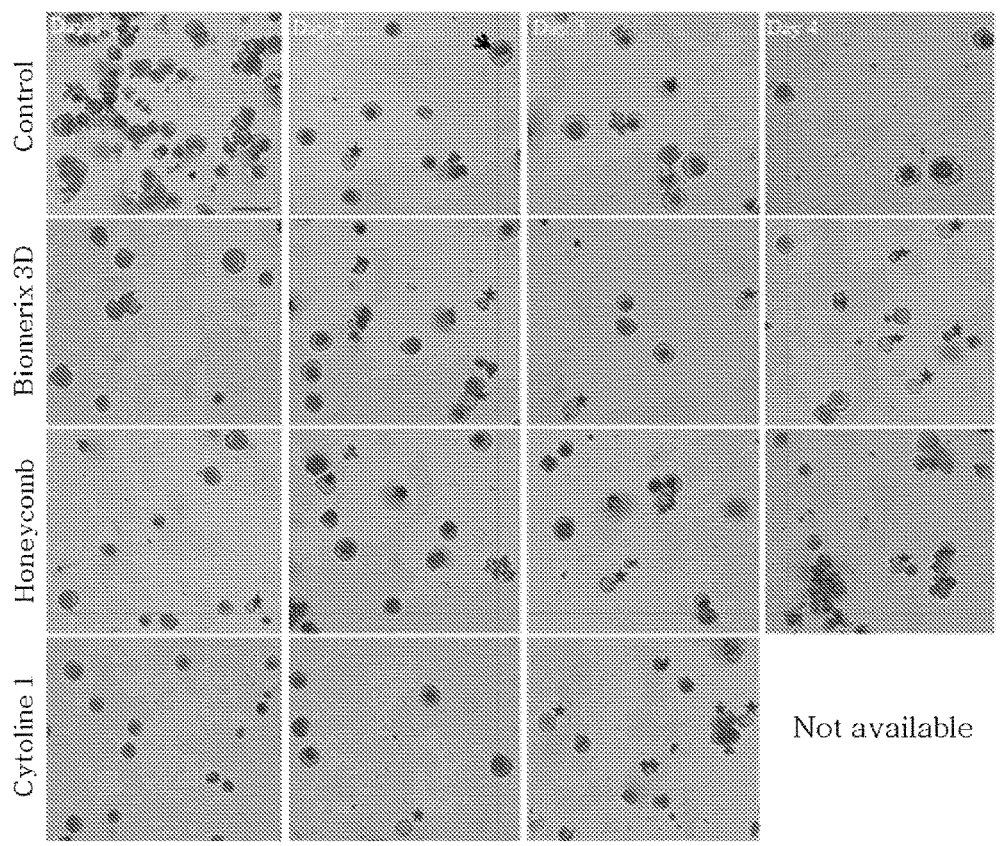
FIG. 19 shows images (×200) observed after 2D high density and 3D packed cell culture of erythroid cells and Wright-Giemsa staining: the red asterisks indicate enucleated erythrocytes; scale bar represents 50 μm.
Figure 20:
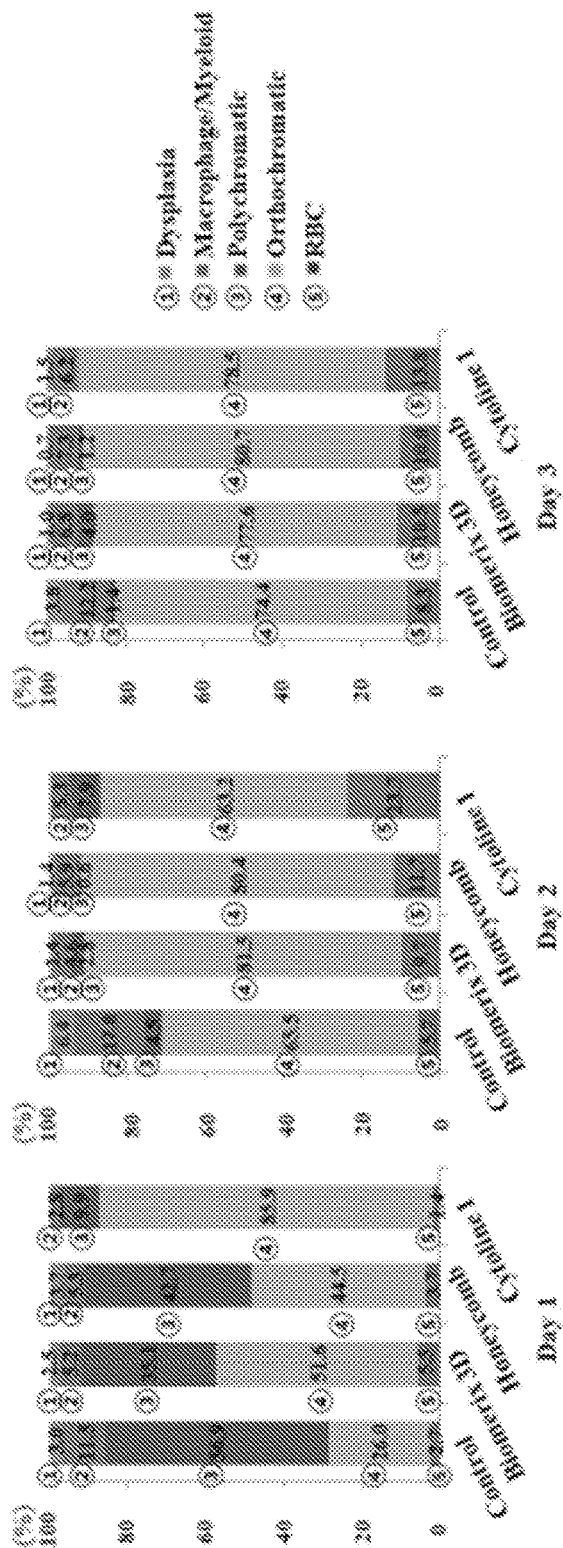
FIG. 20 shows graphs comparing the proportions of erythroid cells at different maturation stages after culture on different porous structures.

During culture for 3 days, fast maturation to erythrocytes was observed in the 3D porous structure compared to in the control. Hemoglobin was accumulated, rendering the color of cell pellets deep red. On day 1 of culture, noticeably red cell pellets were observed in Cytoline 1 than in the other scaffolds. As the days of culture passed, pellets of cultured cells were colored red also in the scaffolds Bioemrix 3D and Honeycomb. Although the maturation rates of cells may vary depending on the kind of the structures, all 3D packed cell culture environments were confirmed to be efficient and suitable for erythrocyte production. FIG. 19 shows images of stained cells (left) and FIG. 20 shows the proportions of cells at different maturation stages. Particularly, as the days of culture increased, the viabilities of cells cultured in the scaffolds Biomerix 3D and Honeycomb were higher than those in the control (see FIG. 18, right) and the number of stained erythrocytes having undergone enucleation increased in Biomerix 3D on day 4 of culture (see FIG. 19).

Figure 21:
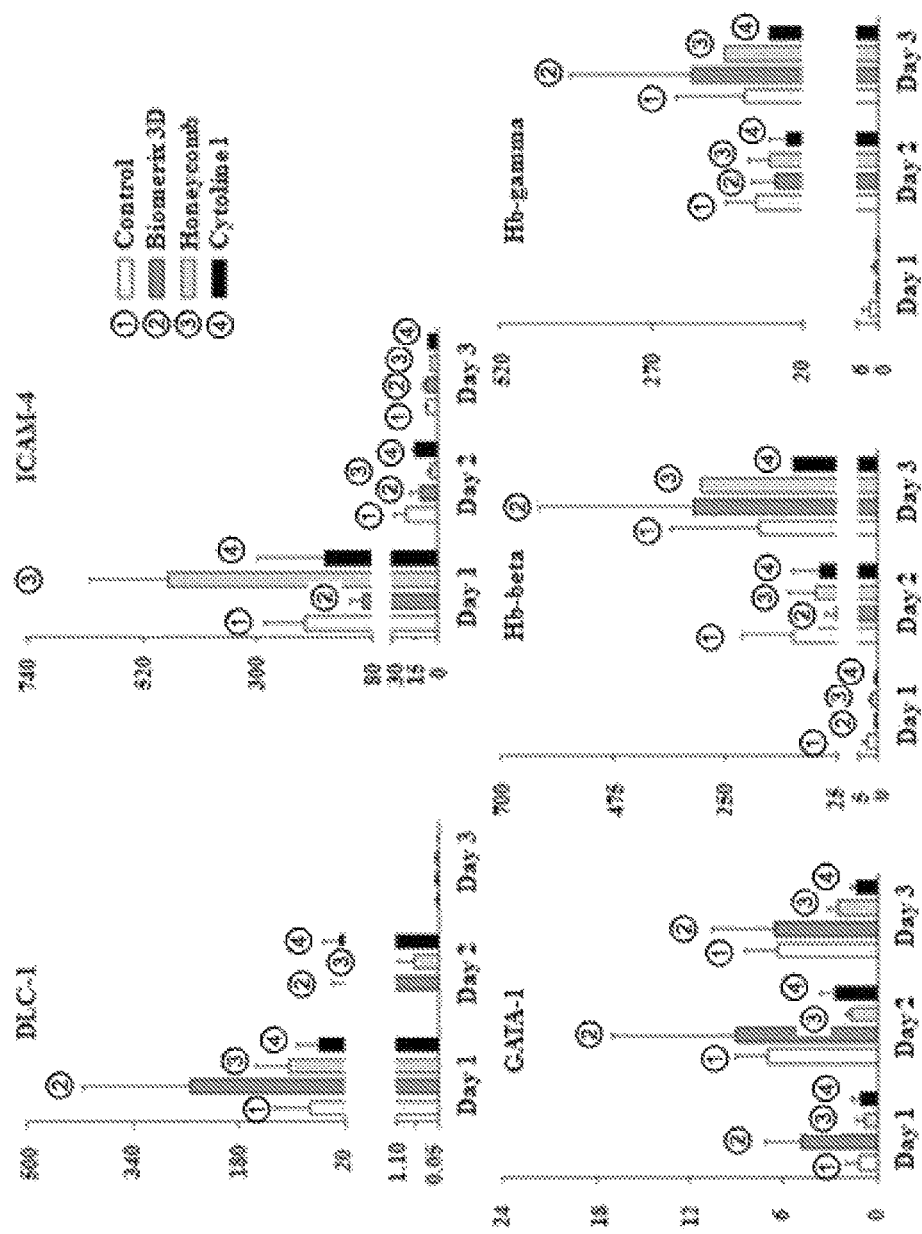
FIG. 21 shows the results obtained by qPCR of erythrocyte production markers (ICAM-4, GATA-I, Hb-beta, and Hb-gamma) and adhesion-related signals (DLC-1 and ICAM-4) after 3D packed cell culture for 3 days.

Cell signaling was analyzed in cells after high density packed cell culture (for 3 days) and were compared with that in cells before culture (0h). The mRNA expression levels of deletion in liver cancer 1 (DLC-I) and intercellular adhesion molecule 4 (ICAM-4) as erythroblast adhesion-related markers, GATA-1 as a transcription factor, and Hb-beta and Hb-gamma as erythroid cell maturation markers were measured (see FIG. 21). On day 1 of culture, the mRNA expression levels of DLC-1 in Biomerix 3D and ICAM-4 were 253.2-fold and 104.9-fold higher than that in the 0h control, respectively. On day 2 of culture The mRNA expression level of GATA-1 increased by 9.1 times in erythroid cells cultured in Biomerix 3D. On day 3 of culture, the mRNA expression levels of Hb-beta increased by 313.0 times and 298.2 times in Biomerix 3D and Honeycomb. On day 3 of culture, the mRNA expression level of Hb-gamma increased by 203.3 times in Biomerix 3D. These results demonstrate that packed cell culture of mature erythroid cells in the porous structures leads to an increase intercellular contact, resulting in greatly enhanced cell adhesion and cell maturation.

10. Measurement of the Ability of Cultured Cells to Transport Oxygen

Figure 22:
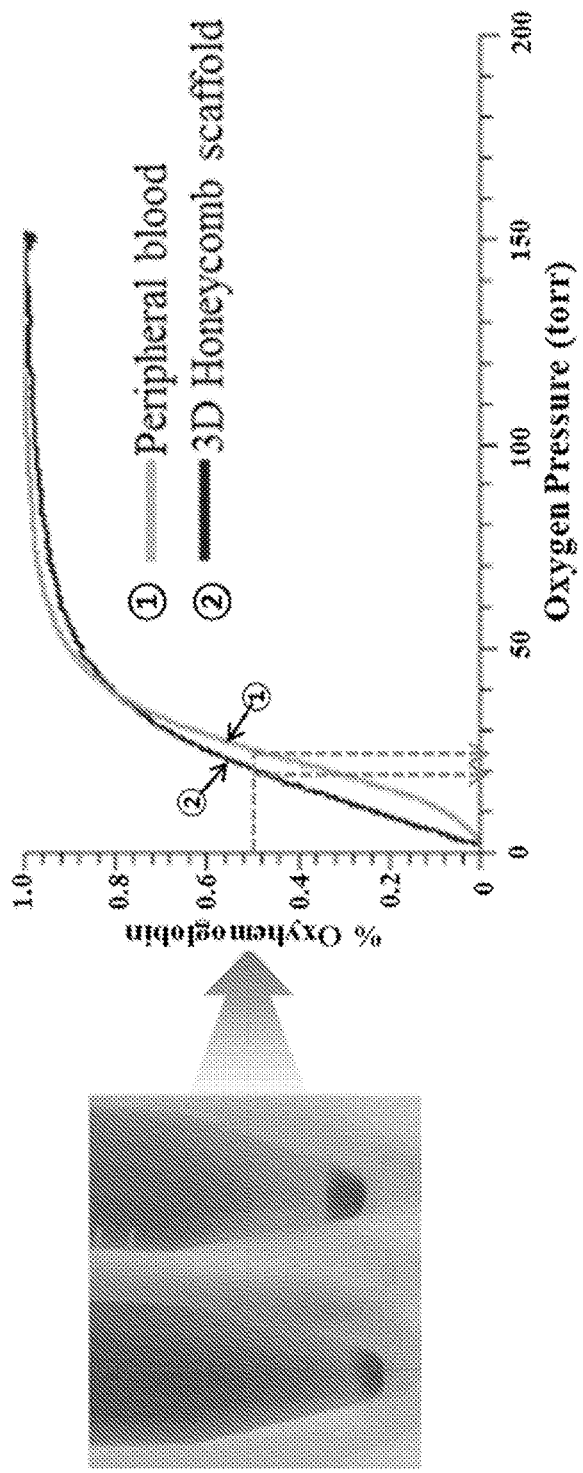
FIG. 22 is a graph showing that in vitro produced erythrocytes were functionally similar to the peripheral blood of a healthy donor.
Figure 23:
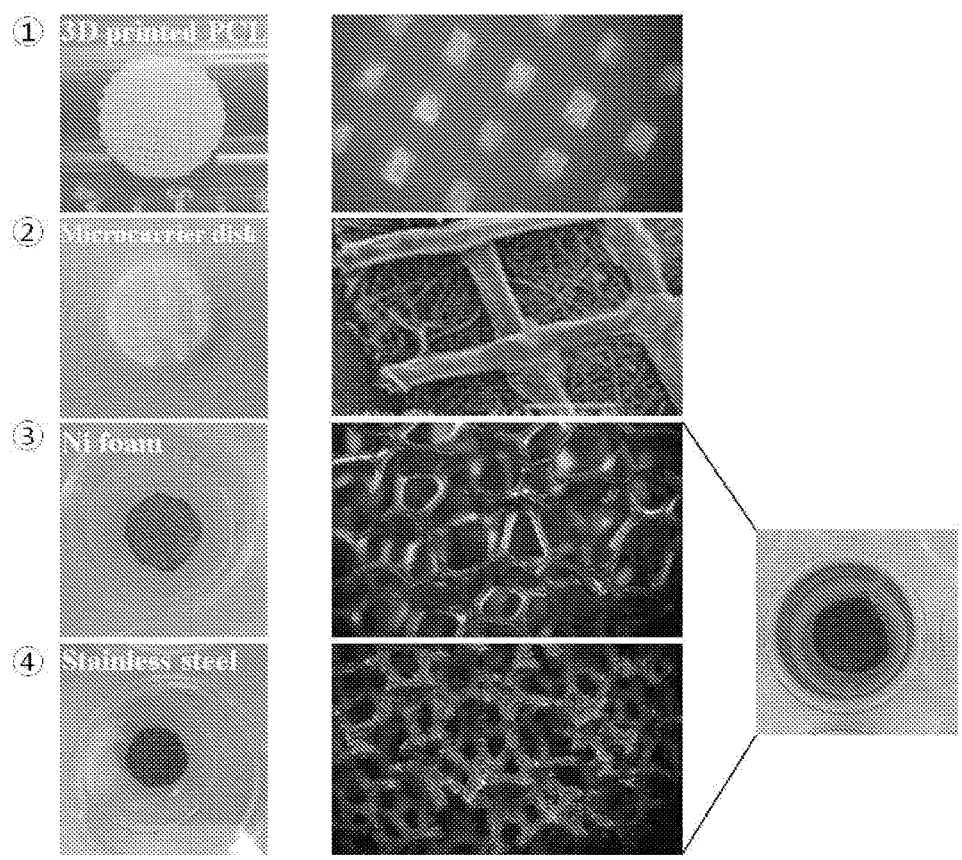
FIG. 23 shows various structures available for 3-dimensional packed cell culture of erythroid cells.

FIG. 22 shows pellets of mature erythrocytes after culture (left). The ability of the mature erythroid cells to transport $O_2$ was confirmed to be similar to that of the control (p50=20.8 and p50=25.8 for produced erythrocytes and control, respectively) (see FIG. 22).

11. Confirmation of Effect of Co-culture with Constituents of Bone Marrow Cells

Erythroid cells were co-cultured with the constituents of bone marrow. As a result, the cell populations were different under the two conditions. Co-culture of all cells in the 3D structure was confirmed to be helpful in the differentiation of erythroid cells (see FIG. 24).

Figure 24:
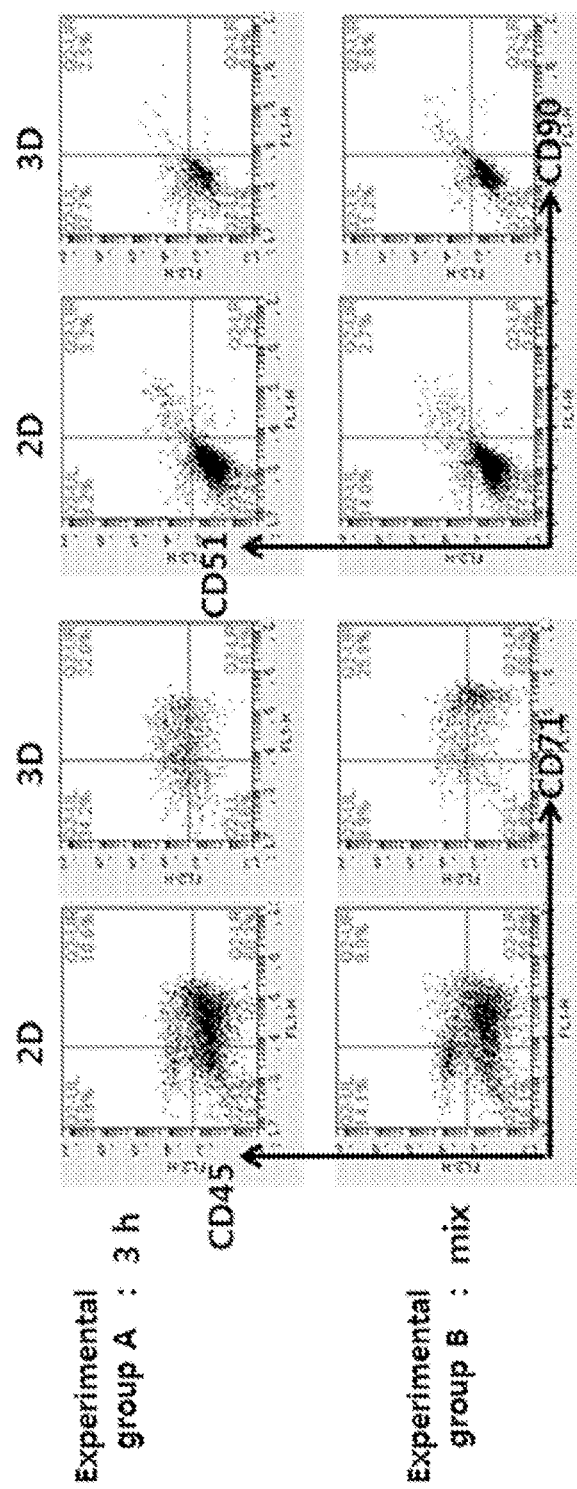
FIG. 24 shows the distributions of cells obtained after adherent cells (MSCs) and osteoblasts were placed in porous structures, allowed to stand for 3 h until cells were adhered to the porous structures, and added with erythroid cells (upper row "3 h"; experimental group A), and the distributions of cells obtained after the three types of cells were added simultaneously and co-cultured for 192 h (lower row "mix"; experimental group B).
Figure 25:
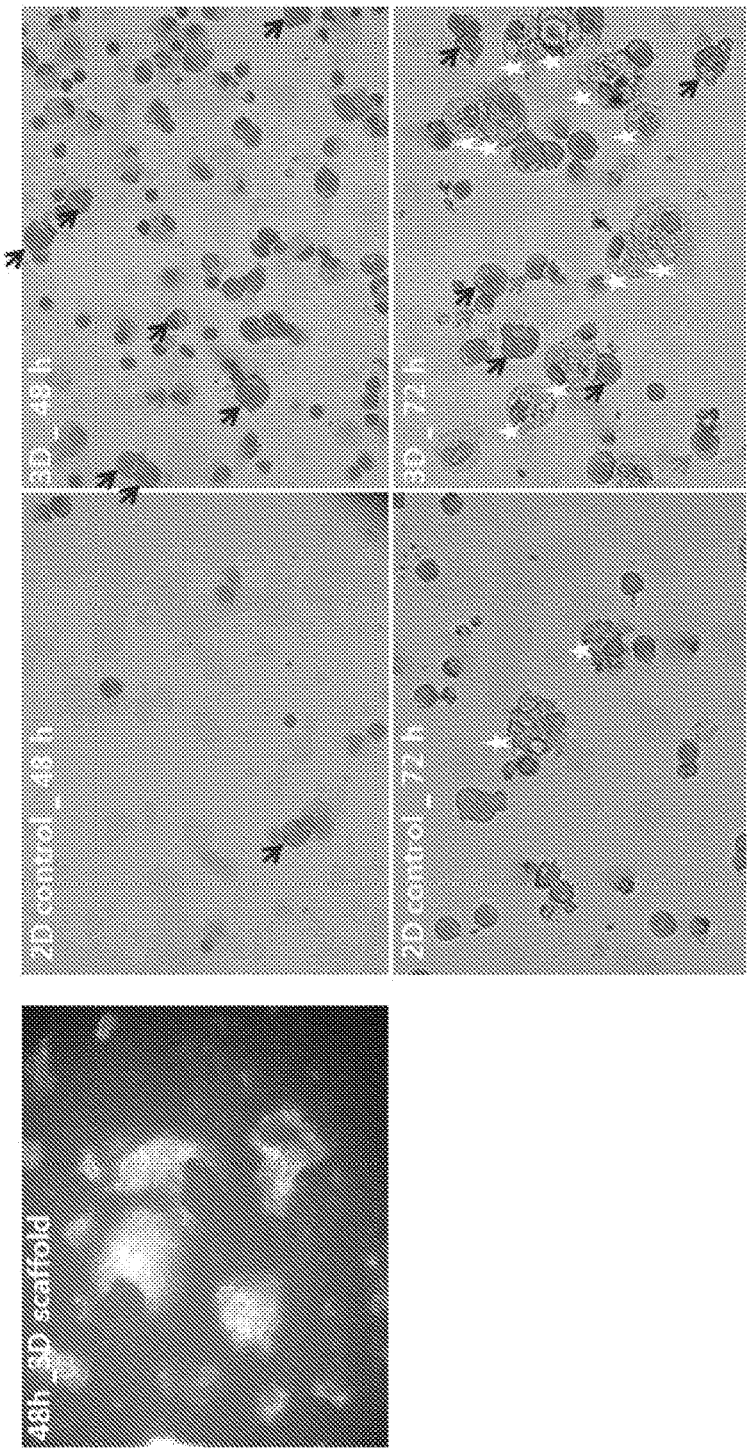
FIG. 25 shows the experimental results obtained after co-culture of myeloid cells including macrophages and monocytes with erythroid cells in 3D porous structures for 72 h. The co-culture induced steric interactions in the porous structures to affect the maturation of erythroid cells and the production of erythroid cells at the terminal maturation stage. The left microscopy image shows the internal morphology of the structure after culture for 48 h and the right images show the stained cells after culture 48 and 72 h (the black arrows, red arrows, and white asterisks indicate immature erythroid cells, mature erythroid cells, and macrophages, respectively, and the remaining cells are monocytes).

FIG. 24 shows the results obtained after co-culture of mature erythroid cells with mesenchymal stem cells (MSCs) and osteoblasts as the cells of bone marrow in the porous structures. In experimental group A, adherent cells MSCs and osteoblasts were placed in the porous structures, allowed to stand for 3 h until cells were adhered to the porous structures, added with erythroid cells, and cultured. In experimental group B, the three types of cells were added simultaneously and co-cultured for 192 h. In the experimental group B where cells were cultured simultaneously, after 192 h, the percent of CD51+CD90+ representing MSCs was increased by 3.1%, which was maintained constant, in 3D culture compared to in 2D culture. The percent of CD45+ CD71+ representing immature erythroid cells was increased by 16.0% and the percent of CD45−CD71+ representing mature erythroid cells was similar to that in the control. In the experimental group A where erythroid cells were added later than adherent cells, after 192 h, the percent of cell markers CD51+CD90+ cells was lower by about 0.7% but the percent of CD45+CD71+ was higher by 21.4% in 3D culture than in 2D culture, revealing that the conditions of experimental group A are effective in maintaining and proliferating erythroid cells in the 3D porous structure. Erythroid cells in bone marrow are attached together 3-dimensionally to create spaces called erythroblastic islands, where they are mature and proliferate. The erythroblastic islands in bone marrow are important spaces where immature erythroid cells closely interact with histiocytes for their maturation. Likewise, the maturation of erythroid cells and the production of final red blood cells could be maximized through co-culture of erythroid cells with myeloid cells including histiocytes and monocytes in the 3D porous structure, which were empirically determined. To this end, bone marrow mononuclear cells (BM MNC) were added at a density of $1 \times 10^8$ cells/mL to a 3D stainless steel porous structure, surrounded with a 3 µm spin filter, and cultured for 72 h (experimental group). The conditions of 2D control, the culture medium, and medium exchange conditions were the same as described above. Cell adhesion and 3D packing in the porous structure were observed using a microscope at 24-h intervals (see FIG. 25, left). The maturation of erythroid cells by steric intercellular interaction in the porous structure was confirmed using Wright-Giemsa staining at the same time intervals (see FIG. 25, right). After 48 h of culture, immature erythroid cells were noticeably observed in the 3D experimental group compared to in the 2D control (the black arrows indicate immature erythroid cells and the remaining cells are mononuclear cells and histiocytes). Also after 72 h of culture, mature erythroid cells and histiocytes were clearly observed in the experimental group compared to in the control (the black arrows indicate immature erythroid cells, the red arrows indicate mature erythrocytes, and the white asterisks indicate histiocytes). This reveals that steric interactions between myeloid cells in the 3D porous structure play an important in the maturation of erythroid cells.

While specific embodiments of the invention have been described in detail, it will be appreciated by those skilled in the art that such detailed descriptions are merely preferred embodiments and the scope of the present invention is not limited thereto. Therefore, the true scope of the present invention should be defined by the appended claims and their equivalents.

REFERENCES

1. Lowe K. Blood substitutes: from chemistry to clinic, *Journal of materials chemistry* 2006; 16: 4189-4196.

2. Timmins N E, Nielsen L K. Blood cell manufacture: current methods and future challenges. *Trends in Biotechnology* 2009; 27: 415-422.

3. Choi H S, Lee E M, Kim H O et al. Autonomous control of terminal erythropoiesis via physical interact ions among erythroid cells. *Stem Cell Res* 2013; 10: 442-453.

4. Kim H O, Baek E J. Red blood cell engineering in stroma and serum/plasma-free conditions and long term storage. *Tissue Eng* Part A 2012; 18: 117-126.

5. Baek E. J., Kim H. S., Kim J. H. et al. Stroma-free mass production of clinical grade red blood cells by using poloxamer 188 as a RBC survival enhancer. Transfusion 2009.

What is claimed is:

1. A method for in vitro expansion of erythroid cells comprising subjecting erythroid cells to 3-dimensional packed cell culture with a porous structure,
    wherein the culture is performed in each pore of the porous structure, and
    wherein the erythroid cells are mixed and co-cultured with cells selected from the group consisting of mesenchymal stem cells, endothelial cells, monocytes, macrophages, and histiocytes during the 3-dimensional packed cell culture.

2. The method according to claim 1, wherein the pores in the porous structure have a size distribution of 30 to 500 µm.

3. The method according to claim 1, wherein the culture is performed in a medium to which shear stress is applied by a continuous flow.

4. The method according to claim 3, wherein the flow is created by stirring.

5. The method according to claim 4, wherein the flow is created by stirring at 1 to 50 rpm.

6. The method according to claim 3, wherein the culture is performed in a filter in the medium to prevent erythrocytes from escaping from the porous structure during the continuous flow.

7. The method according to claim 6, wherein the filter has a mesh size of 1 to 8 µm.

8. The method according to claim 1, wherein the erythroid cells are cells that enter the terminal maturation stage.

9. The method according to claim 1, wherein the erythroid cells express at least one adhesion-related gene selected from deleted in liver cancer 1 (DLC 1), intercellular adhesion molecule-4 (ICAM-4), and very late antigen-4 (VLA-4).

10. The method according to claim 1, wherein the erythroid cells are mixed and co-cultured with mesenchymal stem cells, endothelial cells, monocytes, macrophages, and histiocytes during the 3-dimensional packed cell culture.

11. The method according to claim 1, wherein the ratio of the number of cells selected from the group consisting of mesenchymal stem cells, endothelial cells, monocytes, macrophages, and histiocytes to the number of the erythroid cells is from 1:10 to 2:1.

* * * * *